(12) United States Patent
Hayashizaki et al.

(10) Patent No.: US 6,482,938 B1
(45) Date of Patent: Nov. 19, 2002

(54) COMPOUNDS HAVING ENERGY TRANSFER FUNCTION AND METHOD FOR DNA BASE SEQUENCING BY USING THE SAME

(75) Inventors: Yoshihide Hayashizaki, Ibaraki (JP); Takumi Tanaka, Hyogo (JP)

(73) Assignees: Wako Pure Chemical Industries, Ltd., Osaka (JP); The Institute of Physical & Chemical Research, Saitama (JP)

( * ) Notice: Subject to any disclaimer, the term of this patent is extended or adjusted under 35 U.S.C. 154(b) by 0 days.

(21) Appl. No.: 09/254,547

(22) PCT Filed: Jul. 10, 1998

(86) PCT No.: PCT/JP98/03093

§ 371 (c)(1), (2), (4) Date: Sep. 17, 1999

(87) PCT Pub. No.: WO99/02544

PCT Pub. Date: Jan. 21, 1999

(30) Foreign Application Priority Data

Jul. 11, 1997 (JP) .............................................. 9-186886

(51) Int. Cl.[7] ........................ C07H 19/04; C12Q 1/68; C12P 19/34; C07D 311/78; C07D 311/88

(52) U.S. Cl. ..................... 536/26.6; 435/6; 435/91.1; 435/91.2; 549/224; 549/223; 549/227; 549/225

(58) Field of Search ...................... 435/6, 91.1, 91.2; 536/26.6; 549/224, 223, 227, 225

(56) References Cited

U.S. PATENT DOCUMENTS 5,547,835 A * 8/1996 Koster ........................... 435/6
5,800,996 A   9/1998 Lee et al. ...................... 435/6
5,863,727 A * 1/1999 Lee et al. ...................... 435/6

FOREIGN PATENT DOCUMENTS

EP    805190 A2    5/1997

OTHER PUBLICATIONS

Craig T. Martin et al, "Processivity in Early Stages of Transcription by T7 RNA Polymerase", *Biochemistry 1988*, vol. 27, pp. 3966–3974, The American Chemical Society, Washington, DC USA.

Vladimir D. Axelrod et al, "Transcription from Bacteriophage T7 and SP6 RNA Polymerase Promoters in the Presence of 3'–Deoxyribonucleoside 5'–Triphosphate Chain Terminators", *Biochemistry 1985*, vol. 24 pp. 5716–5723, The American Chemical Society, Washington D.C., USA.

Craig T. Martin et al, "T7 RNA Polymerase Does Not Interact with the 5'–Phosphate of the Initiating Nucleotide", *Biochemistry 1989*, vol. 28, pp. 2760–2762, The American Chemical Society, Washington D.C., USA.

Jingyue et al "Fluorescence energy transfer dye–labeled primers for DNA sequencing and analysis", Proc. Natl. Acad. Sci. USA, vol. 92 (May 1995), p. 4347–4351.

* cited by examiner

*Primary Examiner*—Jezia Riley
(74) *Attorney, Agent, or Firm*—Burns, Doane, Swecker & Mathis, L.L.P.

(57) ABSTRACT

Disclosed are compounds having two kinds of reporters that can be a donor and an acceptor for energy transfer, for example, fluorescent groups, and having a 2', 3'-dideoxyribonucleotide residue or a 3'-deoxyribonucleotide residue. These compounds can be used as terminators for the chain terminator method. The two kinds of reporters are arranged with a distance sufficient for causing energy transfer from the donor to the acceptor. Also disclosed are methods for determining DNA sequences based on the chain terminator method wherein the chain termination reaction is performed by using the above terminators. Also disclosed are compounds having two kinds of reporters that can be a donor and an acceptor for energy transfer, which can be used as a primer or an initiator in methods for determining DNA sequences utilizing the chain terminator method, and methods for determining DNA sequences utilizing the compounds.

40 Claims, 6 Drawing Sheets

SEQUENCE LISTING

<160> NUMBER OF SEQ ID NOS: 14

<210> SEQ ID NO 1
<211> LENGTH: 50
<212> TYPE: DNA
<213> ORGANISM: T7Rpol-N

<400> SEQUENCE: 1
atattttagc catggaggat tgatatatga acacgattaa catcgctaag        50

<210> SEQ ID NO 2
<211> LENGTH: 39
<212> TYPE: DNA
<213> ORGANISM: T7Rpol-C

<400> SEQUENCE: 2
atattttagc catggtatag tgagtcgtat tgatttgcg                    39

<210> SEQ ID NO 3
<211> LENGTH: 26
<212> TYPE: DNA
<213> ORGANISM: PCR primer F646Y(+)

<400> SEQUENCE: 3
gttgacggaa gccgtactct ttggac                                  26

<210> SEQ ID NO 4
<211> LENGTH: 26
<212> TYPE: DNA
<213> ORGANISM: PCR primer F646Y(-)

<400> SEQUENCE: 4
gtccaaagag tacggcttcc gtcaac                                  26

<210> SEQ ID NO 5
<211> LENGTH: 23
<212> TYPE: DNA
<213> ORGANISM: T7RNAP-HpaI-N

<400> SEQUENCE: 5
cgcgcggtta acttgcttcc tag                                     23

<210> SEQ ID NO 6
<211> LENGTH: 23
<212> TYPE: DNA
<213> ORGANISM: pTrc99a-PstI-C

<400> SEQUENCE: 6
gcatgcctgc aggtcgactc tag                                     23

<210> SEQ ID NO 7
<211> LENGTH: 21
<212> TYPE: DNA
<213> ORGANISM: primer ApaF1

<400> SEQUENCE: 7
catctggtcg cattgggtca c                                       21

<210> SEQ ID NO 8
<211> LENGTH: 21
<212> TYPE: DNA
<213> ORGANISM: primer Xho-R

```
<400> SEQUENCE: 8
ccaagtgttc tcgagtggag a                                           21

<210> SEQ ID NO 9
<211> LENGTH: 26
<212> TYPE: DNA
<213> ORGANISM: primer Xho-F

<400> SEQUENCE: 9
ctaagtctcc actcgagaac acttgg                                      26

<210> SEQ ID NO 10
<211> LENGTH: 21
<212> TYPE: DNA
<213> ORGANISM: primer AflII-R

<400> SEQUENCE: 10
cagccagcag cttagcagca g                                           21

<210> SEQ ID NO 11
<211> LENGTH: 21
<212> TYPE: DNA
<213> ORGANISM: primer Xho-R and primer 667R

<400> SEQUENCE: 11
gctgagtgta catcggaccc t                                           21

<210> SEQ ID NO 12
<211> LENGTH: 21
<212> TYPE: DNA
<213> ORGANISM: primer 667F and primer AflIIR

<400> SEQUENCE: 12
gctgagtgta catcggaccc t                                           21

<210> SEQ ID NO 13
<211> LENGTH: 79
<212> TYPE: DNA
<213> ORGANISM: Dye-terminator
<220> FEATURE:
<221> NAME/KEY: misc_feature
<222> LOCATION: (32)..(46)
<223> OTHER INFORMATION: Nucleotides at positions 32 and 46 are n
      wherein n = any nucleotide.

<400> SEQUENCE: 13
tcccccggct gcaaggattc gatacaagct tnaggttaac gtgganctcg agggggggcc   60
ggctacaggg cttttgttc                                               79

<210> SEQ ID NO 14
<211> LENGTH: 73
<212> TYPE: DNA
<213> ORGANISM: ET-terminator: x10 dilution

<400> SEQUENCE: 14
tcccccggct gcaggattcg atacaactta cgatacgtcg actcgagggg gggccggcta   60 aggcttttg ttc                                                      73
```

COMPOUNDS HAVING ENERGY TRANSFER FUNCTION AND METHOD FOR DNA BASE SEQUENCING BY USING THE SAME

CONTINUING APPLICATION DATA

This application is a 371 of PCT/JP98/03093, filed Jul. 10, 1998.

1. Technical Field

The present invention relates to compounds having energy transfer function, and DNA sequence determination methods utilizing the compounds as a terminator, a primer or an initiator.

2. Background Art

There have been known methods for determining nucleotide sequences by preparing chain termination reaction products using a DNA polymerase or RNA polymerase, and subjecting them to separation and fractionation. Further, it has been tried to develop quicker nucleotide sequence determination methods in such ongoing projects as for elucidating gene sequences of higher animals. Some of such methods utilize a DNA fluorescence sequencer where sequencing reaction products obtained by using a fluorescence-labeled terminator are separated and fractionated by electrophoresis, the resulting DNA fragments are excited by a laser, and the emitted fluorescence is detected to determine nucleotide sequences.

It has been also known that quantum yield of fluorescent dyes can be increased based on the principle of energy transfer by using two fluorescent dyes (a donor dye and an acceptor dye). Recently, energy transfer primers have been developed which are composed of an oligonucleotide having covalently bonded two fluorescent dyes and used as a primer for sequencing reactions based on the principle of energy transfer [see, for example, Nature Medicine, 2, 246–249 (1996), WO95/21266, Japanese Patent Unexamined Publication (KOKAI) No. Hei 10-88124/1998 etc.].

In order to realize faster DNA sequencing, systems capable of analyzing multiple samples simultaneously have been developed. In particular, the capillary fluorescence sequencer has an ideal structure, in which loading of samples can be easily automated, and multiple capillaries can be easily used without crossing of lanes. For this fluorescence sequencer, two kinds of optical systems have been used in order to realize the use of larger number of capillaries.

One is the scanning method, and the other is the imaging method. For the both cases, it is essential for the use of larger number of capillaries that a highly sensitive detector, which can detect even a small amount of DNA, should be available. In the scanning method, in order to finish the sequencing within a certain period of time regardless of the number of capillaries, time assigned to each capillary should be shorter if the number of capillaries became larger. Therefore, a detector of higher sensitivity is required. In the imaging method, the range of the field covered by a detector is constant regardless of the number of capillaries. In order to use a larger number of capillaries, it is necessary to increase the number of picture elements of optics element, and decrease the diameter of each capillary. Therefore, it also requires a detector having higher sensitivity.

On the other hand, as discussed above, the technique for utilizing the fluorescence primer based on the principle of energy transfer for DNA sequencing has been developed in order to increase DNA detection sensitivity. However, because the technique utilizes the fluorescence primer, it requires complex operation procedure of which termination reaction should be performed for each of the four kinds of bases, A, G, C and T, and the mixed sequencing reaction products should be subjected to electrophoresis. In addition, because the sequencing based on the transcription reaction by a promoter-dependent RNA polymerase does not use a primer, the energy transfer primer cannot be used in it.

In order to realize faster DNA sequencing, it is necessary to use a highly sensitive detection system with high quantum yield such as energy transfer in a multiple capillary sequencer. On the contrary, however, the systems utilizing the energy transfer primers suffers from technical limitations such as complicated pretreatment (DNA polymerase system) and necessity of primer itself (RNA polymerase system).

Therefore, an object of the present invention is to provide a means which eliminates the drawbacks of the systems utilizing the energy transfer primers, i.e., which is adaptable to the transcription reaction systems utilizing RNA polymerases, and enables sequencing methods capable of high sensitivity detection utilizing the energy transfer and not requiring the complicated procedure consisting of mixing of the four kinds of reaction products for A, G, C and T separately obtained in the preliminary processes.

In particular, an object of the present invention is to provide a compound which can utilize the principle of energy transfer to afford high sensitivity, and a method for determining nucleotide sequences of DNA which utilizes such a compound as mentioned above as a terminator, and can detect labeled DNA fragments with high sensitivity based on the chain terminator method.

Meanwhile, the energy transfer primer disclosed in WO95/21266 is composed of two reporters causing the energy transfer which are connected with a part of oligonucleotide constituting the primer used as a linker. However, such a primer is practically disadvantageous, because a distinct primer must be synthesized for each of oligonucleotides used as primers having different sequences. On the other hand, the energy transfer primer of Japanese Patent Unexamined Publication (KOKAI) No. Hei 10-88124/1998 is composed of two reporters connected with an aliphatic or aromatic residue used as a linker. Therefore, it does not suffer from the problem observed in the primer of WO95/21266, but it may suffers from another problem that, when a longer linker is desired to realize a longer distance between the two reporters, it may be difficult to obtain a desired distance between the two reporters because of the bonding scheme of the linker even though the linker has a long chain.

Therefore, another object of the present invention is to provide a compound useful as the energy transfer primer which solves the above problem, i.e., which does not use a part of a primer sequence as the linker and enables easy control of the distance between the two reporters.

A further object of the present invention is to provide a method for determining nucleotide sequences of DNA which uses the above compound as the energy transfer primer.

In a method for determining nucleotide sequences using a terminator, an RNA polymerase such as T7 RNA polymerase is used for a reaction in a mixture of ribonucleoside 5'-triphosphates and 3'-deoxyribonucleotides. In this reaction, ribonucleotides and 3'-deoxyribonucleotides having a base corresponding to the sequence of the template are sequentially incorporated into a ribonucleotide sequence to synthesize a polyribonucleotide sequence. The resulting polyribonucleotides (nucleic acid transcription products) are then separated, and nucleic acid sequence is read from the resulting separated fractions to determine the nucleotide sequence of the DNA. For example, fluorescence-labeled 3'-dNTP derivatives are used as the terminators of the nucleic acid transcription for the nucleotide sequence determination.

However, terminators composed of 3'-dNTP having various kinds of labels may be difficult to be incorporated into a nucleic acid sequence, depending on the kind of the labels and the bonding scheme of the labels. In particular, when the chain length becomes longer, such a tendency becomes more serious. To deal with this problem, the nucleotide sequence may also be determined by using unlabeled compounds as the terminators and labeled initiators. Also in such a case, sensitivity of the label is important like in the labeled terminators mentioned above.

Therefore, a further object of the present invention is to provide a compound having energy transfer function which can be used as an initiator (transcription initiator) in a method for determining nucleotide sequences of DNA using an RNA polymerase without using a labeled terminator for the nucleotide sequence determination.

A still further object of the present invention is to provide a method for determining DNA sequences utilizing the above compound as an energy transfer initiator.

SUMMARY OF THE INVENTION

The present invention relates to a compound represented by the following general formula (1):

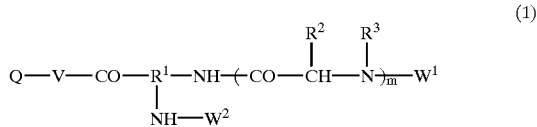

(1)

wherein Q represents a mono- or oligonucleotide residue, V represents —C≡C—$(CH_2)_{n1}$—NH— or —CH=CH—$(CH_2)_{n2}$—NH— wherein n1 and n2 represent an integer not less than 1, $R^1$ represents a trivalent group, $R^2$ and $R^3$ independently represent hydrogen atom or a hydrocarbon residue, or $R^2$ and $R^3$ may join to form a ring together with the adjacent CH and NH, $W^1$ and $W^2$ independently represent a fluorescent group, and m represents an integer not less than 1.

In the above compound, $R^2$, $R^3$ and m are preferably selected so that the distance between $W^1$ and $W^2$ should be within the range of 10–100 Å.

In the above compound, Q is preferably a 2', 3'-dideoxyribonucleotide residue or a 3'-deoxyribonucleotide residue. Such a compound can be used as a terminator for the DNA sequence determination method based on the chain terminator method.

The present invention relates to a method for determining DNA sequences based on the chain terminator method, characterized in that the chain termination reaction is performed by using a compound represented by the general formula (1) where Q is a 2',3'-dideoxyribonucleotide residue or a 3'-deoxyribonucleotide residue as a terminator.

This method includes a method using DNA polymerase and a compound represented by the general formula (1) where Q is a 2',3'-dideoxyribonucleotide residue as the terminator, and a method using RNA polymerase and a compound represented by the general formula (1) where Q is a 3'-deoxyribonucleotide residue as the terminator.

In this method, four kinds of compounds corresponding to four kinds of bases are used as terminators, wherein the compounds are selected from the compounds represented by the general formula (1) and each of which has one of different four kinds of fluorescent groups as at least one of $W^1$ and $W^2$, and the chain termination reaction using the above four kinds of compounds can be performed in the same reaction system.

The present invention relates to a compound represented by the general formula (1) where Q is an oligonucleotide residue having a 2'-deoxyribonucleotide residue at its end. This compound can be used as a primer in the DNA sequence determination method based on the primer method.

The present invention further relates to a method for determining DNA sequences based on the primer method, characterized in that the above compound is used as a primer. In this method, an unlabeled terminator can be used.

The present invention relates to a compound represented by the general formula (1) where Q is a mono- or oligonucleotide residue not having a phosphate group, or having a mono- or diphosphate group at the 5' end. This compound can be used as an initiator in DNA sequence determination methods based on the chain terminator method.

The present invention relates to a method for determining DNA sequences based on the chain terminator method, characterized in that the chain termination reaction is performed by using an initiator comprising a mono- or oligonucleotide residue not having a phosphate group, or having a mono- or diphosphate group at the 5' end and two kinds of reporters that can be a donor and an acceptor of energy transfer, and an RNA polymerase.

In this method, the compound represented by the general formula (1) where Q is a mono- or oligonucleotide residue not having a phosphate group, or having a mono- or diphosphate group at the 5' end can be used as an initiator. As the terminator, an unlabeled terminator can be used.

The present invention further relates to a method for determining DNA sequences based on the chain terminator method characterized in that the chain termination reaction is performed by using a terminator comprising a 3'-deoxyribonucleotide residue and two kinds of reporters that can be a donor and an acceptor of energy transfer, and an RNA polymerase.

In this method, two reporters on the terminator are preferably arranged with a distance sufficient for causing energy transfer from the donor to the acceptor. The distance sufficient for causing energy transfer from the donor to the acceptor is, for example, in the range of 10–100 Å. The reporters are, for example, selected from the group consisting of fluorescent groups, phosphorescent groups, spin-labeled groups and groups having high electron density.

In this method, for example, the donor contained in the terminator is selected from the group consisting of fluorescein dyes, rhodamine dyes and 4,4-difluoro-4-bora-3a,4a-diaza-s-indacene dyes, and the acceptor is selected from the group consisting of fluorescein dyes, rhodamine dyes and 4,4-difluoro-4-bora-3a,4a-diaza-s-indacene dyes.

In this method, four kinds of terminators corresponding to the four kinds of bases are used as the acceptor, provided that each of which terminators has one of different four kinds of reporters. And the chain termination reaction with the above four kinds of terminators can be performed in the same reaction system.

In the above nucleotide sequence determination methods of the present invention, the chain termination reaction is preferably performed in the presence of inorganic pyrophosphatase.

PREFERRED EMBODIMENTS OF THE INVENTION

Compounds of the Invention

Figure 1:
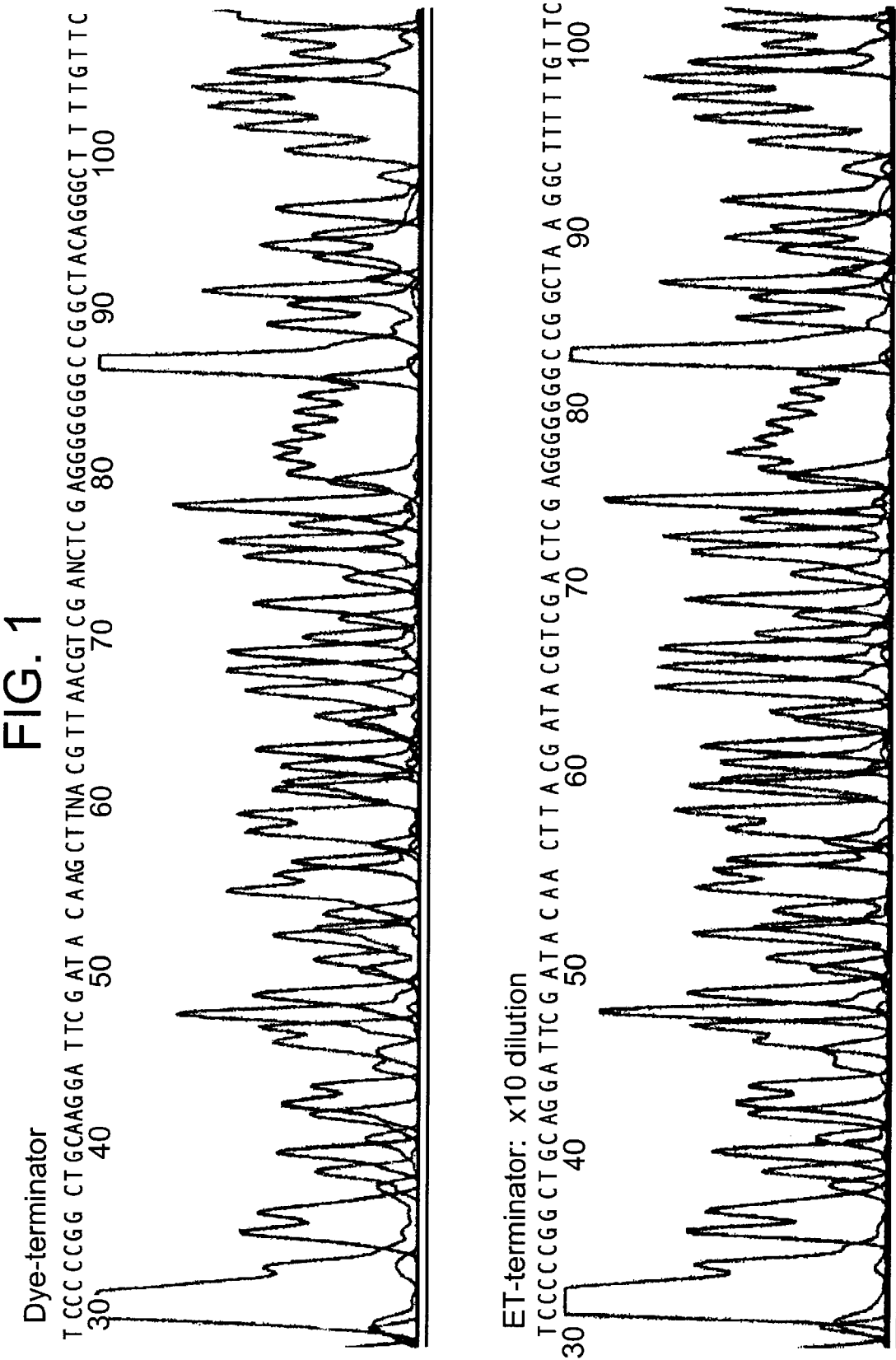
FIG. 1 [SEQ ID NOS. 13–14] shows sequence patterns provided in Example 5.

In the compounds represented by the general formula (1), Q represents a mono- or oligonucleotide residue. More specifically, Q can be, for example, a nucleotide residue such as ribonucleotide residues, 2',3'-dideoxyribonucleotide residues, 2'-deoxyribonucleotide residues, 3'-deoxyribonucleotide residues, and 5'-deoxyribonucleotide residues. Those compounds wherein Q is a 2',3'-dideoxyribonucleotide residue or 3'-deoxyribonucleotide residue can be used as the terminator in the DNA sequence determination methods based on the chain terminator method. In particular, those compounds wherein Q is a 2',3'-dideoxyribonucleotide residue are used as the terminator in the methods using DNA polymerases. Those compounds where Q is a 3'-deoxyribonucleotide residue are used as the terminator in the methods using RNA polymerases. As the 2',3'-dideoxyribonucleotide residue and the 3'-deoxyribonucleotide residue, purine nucleotide residues represented by the following general formulae (2) and (3), and pyrimidine nucleotide residues represented by the following general formula (4) and (5) can be mentioned.

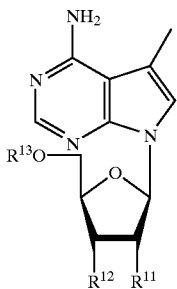

(2)

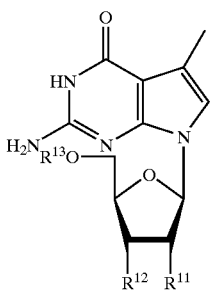

(3)

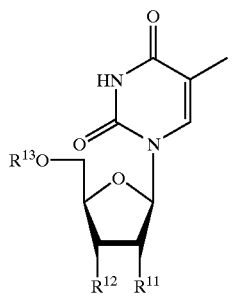

(4)

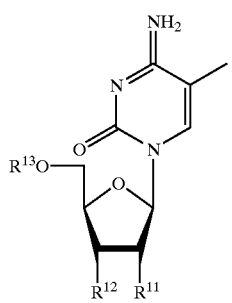

(5)

In the above formulae, both of $R^{11}$ and $R^{12}$ may be hydrogen atoms, or $R^{11}$ can be hydroxyl group and $R^{12}$ can be hydrogen atom. $R^{13}$ can be —$PO_3H_2$, —$P_2O_6H_3$, —$P_3O_9H_4$ or a salt thereof. Examples of the salt include alkali metal salts such as sodium salts, potassium salts, and lithium salts, alkaline earth metal salts such as barium salts, ammonium salts, organic amine salts such as triethylammonium salts, and pyridine salts and the like.

Q can also be an oligonucleotide residue. Those compounds where Q is an oligonucleotide residue, in particular, those compounds comprising an oligonucleotide residue having 2'-deoxyribonucleotide at its end can be used as a primer in DNA sequence determination methods based on the primer method. Nucleotide sequence and size of the oligonucleotide residue can be suitably selected considering the function as the primer, and the size is, for example, in the range of 5–30 nucleotides, preferably 10–30 nucleotides.

Q can also be a mono- or oligonucleotide residue not having a phosphate group, or having a mono- or diphosphate group at the 5' end. Such compounds can be used as an initiator in the DNA sequence determination methods based on the chain terminator method. The mono- or oligonucleotide residue not having a phosphate group, or having a mono- or diphosphate group at the 5' end can be selected from, for example, the group consisting of ribonucleoside residues, ribonucleoside 5'-monophosphate residues, ribonucleoside 5'-diphosphate residues, oligoribonucleotide residues represented by the general formula $N^1(N)_n$ wherein $N^1$ is a ribonucleoside, ribonucleoside 5'-monophosphate or ribonucleoside 5-diphosphate, N is ribonucleoside 5'-monophosphate, and n is an integer not less than 1, and oligoribonucleotide residues represented by the general formula $N^2(N)_n$ wherein $N^2$ is a group represented by the following formula (6), N is a ribonucleoside 5'-monophosphate, and n is an integer not less than 1:

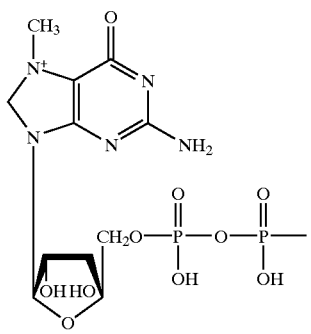

(6)

More specifically, examples of the above mono- or oligoribonucleotide residue include residues of guanosine, guanosine 5'-monophosphate (GMP), guanosine 5'-diphosphate (GDP), oligoribonucleotides represented by the general formula $N^1(N)_{n-1}G$ wherein $N^1$ is a ribonucleoside, ribonucleoside 5'-monophosphate or ribonucleoside 5'-diphosphate, N is a ribonucleoside 5'-monophosphate, n is an integer not less than 1, and G is guanosine 5'-monophosphate, and oligoribonucleotides represented by the general formula $N^2(N)_{n-1}G$ wherein $N^2$ is a group represented by the aforementioned formula (6), N is a ribonucleoside 5'-monophosphate, n is an integer not less than 1, and G is guanosine 5'-monophosphate.

Specific examples of the above mono- or oligoribonucleotide residue further include residues of adenosine, adenosine 5'-monophosphate (AMP), adenosine 5'-diphosphate (ADP), oligoribonucleotides represented by the general formula $N^1(N)_{n-1}A$ wherein $N^1$ is a ribonucleoside, ribonucleoside 5'-monophosphate or ribonucleoside 5'-diphosphate, N is a ribonucleoside 5'-monophosphate, n is an integer not less than 1, and A is adenosine 5'-monophosphate, and oligoribonucleotides represented by the general formula $N^2(N)_{n-1}A$ wherein $N^2$ is a group represented by the aforementioned formula (6), N is a ribonucleoside 5'-monophosphate, n is an integer not less than 1, and A is adenosine 5'-monophosphate.

Specific examples of the above mono- or oligoribonucleotide residue further include residues of cytidine, cytidine 5'-monophosphate (CMP), cytidine 5'-diphosphate (CDP), oligoribonucleotides represented by the general formula $N^1(N)_{n-1}C$ wherein $N^1$ is a ribonucleoside, ribonucleoside 5'-monophosphate or ribonucleoside 5'-diphosphate, N is a ribonucleoside 5'-monophosphate, n is an integer not less than 1, and C is cytidine 5'-monophosphate, and oligoribonucleotides represented by the general formula $N^2(N)_{n-1}C$ wherein $N^2$ is a group represented by the aforementioned formula (6), N is a ribonucleoside 5'-monophosphate, n is an integer not less than 1, and C is cytidine 5'-monophosphate.

Specific examples of the above mono- or oligoribonucleotide residue further include residues of uridine, uridine 5'-monophosphate (UMP), uridine 5'-diphosphate (UDP), oligoribonucleotides represented by the general formula $N^1(N)_{n-1}U$ wherein $N^1$ is a ribonucleoside, ribonucleoside 5'-monophosphate or ribonucleoside 5'-diphosphate, N is a ribonucleoside 5'-monophosphate, n is an integer not less than 1, and U is uridine 5'-monophosphate, and oligoribonucleotides represented by the general formula $N^2(N)_{n-1}U$ wherein $N^2$ is a group represented by the aforementioned formula (6), N is a ribonucleoside 5'-monophosphate, n is an integer not less than 1, and U is uridine 5'-monophosphate.

In the above general formulae $N^1(N)_n$, $N^1(N)_{n-1}G$, $N^1(N)_{n-1}A$, $N^1(N)_{n-1}C$, $N^1(N)_{n-1}U$, $N^2(N)_n$, $N^2(N)^{n-1}G$, $N^2(N)_{n-1}A$, $N^2(N)_{n-1}C$, and $N^2(N)_{n-1}U$, the bases of the ribonucleosides, ribonucleoside 5'-monophosphates and ribonucleoside 5'-diphosphates represented by $N^1$ are not particularly limited, and can be suitably selected from guanine, adenine, cytosine, and uridine, and they are preferably guanine. The kind of the bases of the ribonucleoside 5'-monophosphates represented by N and the sequence when n is 2 or more are also not particularly limited. While n is not particularly limited from the viewpoint of the function of initiator, it is practically 10 or less, preferably 5 or less, more preferably 1 or 2.

In the compounds of the present invention represented by the general formula (1), V represents $-C\equiv C-(CH_2)_{n1}-NH-$ or $-CH=CH-(CH_2)_{n2}-NH-$. n1 and n2 represent an integer not less than 1. One of the end carbon atoms of $-C\equiv C-$ or $-CH=CH-$ in V is bound to the aforementioned mono- or oligonucleotide residue represented by Q at the 5-position for pyrimidine nucleotide residues, or the 7-position for purine nucleotide residues.

Examples of the methylene chain represented by the above $-(CH_2)_{n1}-$ and $-(CH_2)_{n2}-$ include methylene chains where n1 and n2 are 1–15, specifically, a methylene group, an ethylene group, a trimethylene group, a tetramethylene group, a pentamethylene group, a hexamethylene group, a heptamethylene group, an octamethylene group, a nonamethylene group, a decamethylene group and the like.

However, when the compounds are used as terminators for the sequencing reaction by RNA polymerases, n1 and n2 are preferably 4 or more, more preferably n1 and n2 are 4–10, particularly preferably n1 and n2 are 4–8, from the viewpoint of higher incorporation efficiency using RNA polymerases. When the compounds are used as terminators for the sequencing reaction using DNA polymerases, n1 and n2 are preferably 3 or more, more preferably n1 and n2 are 3–10, from the viewpoint of higher incorporation efficiency by DNA polymerases. When the compounds are used as a primer or an initiator, n1 and n2 are suitably selected considering activity of DNA polymerase or RNA polymerase used for the sequencing reaction.

$R^1$ represents a trivalent group, and examples thereof include

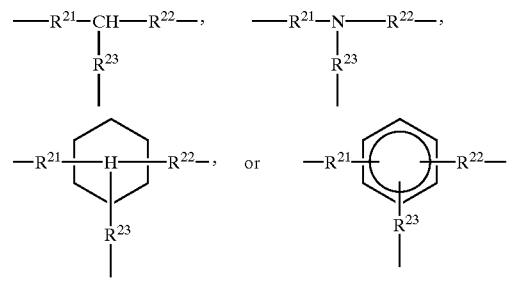

wherein $R^{21}$–$R^{23}$ each independently represent a single bond or a divalent hydrocarbon residue.

The above divalent hydrocarbon residue may be aliphatic, aromatic, or a combination thereof. The divalent aliphatic hydrocarbon residue may be linear, branched or cyclic. Examples of the linear or branched aliphatic divalent hydrocarbon residue include divalent aliphatic hydrocarbon residues having 1–6 carbon atoms, specifically, a methylene group, an ethylidene group, a 1,2-ethanediyl group, a propylidene group, a 1,2-propanediyl group, a 1,3-propanediyl group, an isopropylidene group, a butylidene group, a 1,2-a butanediyl group, a 1,3-butanediyl group, a 1,4-butanediyl group, a 2-methyl-1,2-propanediyl group, a 2-methy-1,3- propanediyl group, a pentylidene group, a 1,2-pentanediyl group, a 1,3-pentanediyl group, a 1,4-pentanediyl group, a 1,5-pentanediyl group, a 2,3-pentanediyl group, a 2,4-pentanediyl group, a 2-methyl-1,2-butanediyl group, a 2-methyl-1,3-butanediyl group, a 2-methyl-1,4-butanediyl group, a 2-methyl-1,5-butanediyl group, a 2-methyl-2,3-butanediyl group, a 2-methyl-2,4-butanediyl group, a 2,2-dimethyl-1,3-propanediyl group, a hexylidene group, a 1,2-hexanediyl group, a 1,3-hexanediyl group, a 1,4-hexanediyl group, a 1,5-hexanediyl group, a 1,6-hexanediyl group, a 2,3-hexanediyl group, a 2,4-hexanediyl group, a 3,4-hexanediyl group and the like. Among these, divalent aliphatic hydrocarbon residues having 1–4 carbon atoms are preferred. As the divalent cyclic aliphatic hydrocarbon residue, for example, divalent cyclic aliphatic hydrocarbon residues having 3–7 carbon atoms can be mentioned. And specific examples thereof include a 1,2-cyclopropanediyl group, a 1,2-cyclobutanediyl group, a 1,3-cyclobutanediyl group, a 1,2-cyclopentanediyl group, a 1,3-cyclopentanediyl group, a 1,2-cyclohexanediyl group, a 1,3-cyclohexanediyl group, a 1,4-cyclohexanediyl group, a 1,2-cycloheptanediyl group, a 1,3-cycloheptanediyl group, a 1,4-cycloheptanediyl group and the like. Among these, divalent aliphatic hydrocarbon residues having 5–7 carbon atoms are preferred. As the divalent aromatic hydrocarbon residues, there can be mentioned, for example, a phenylene group, a biphenylene group, a triphenylene group and the like.

$R^2$ and $R^3$ each independently represent hydrogen atom or a hydrocarbon residue, or $R^2$ and $R^3$ may join to form a ring together with the adjacent CH and NH. Examples of the hydrocarbon residue include linear, branched or cyclic aliphatic hydrocarbon residues having 1–6 carbon atoms such as a methyl group, an ethyl group, a n-propyl group, an isopropyl group, a n-butyl group, an isobutyl group, a tert-butyl group, a sec-butyl group, a n-pentyl group, an isopentyl group, a tert-pentyl group, a 1-methylpentyl group, a n-hexyl group, an isohexyl group, a cyclopropyl group, a cyclopentyl group, and a cyclohexyl group; aralkyl groups having 7–10 carbon atoms such as a benzyl group, a phenethyl group, a phenylpropyl group, and a methylbenzyl group; and aryl groups such as a phenyl group, a tolyl group, a xylyl group, a naphthyl group, and a biphenyl group. Examples of the ring formed by joined $R^2$ and $R^3$ together with the adjacent CH and NH include 3- to 6-membered rings which may contain N and O, specifically, an aziridine ring, an azetidine ring, a pyrrolidine ring, a pyrroline ring, an imidazolidine ring, an imidazoline ring, a pyrazolidine ring, a pyrazoline ring, a piperidine ring, a piperazine ring, a morpholine ring and the like. The repetition number m represents an integer not less than 1.

For the compounds of the present invention, $R^2$, $R^3$ and m are preferably selected so that the distance between $W^1$ and $W^2$ should be in the range of 10–100 Å. The signal such as fluorescence resulting from the energy transfer varies depending on the distance between $W^1$ and $W^2$. The distance between $W^1$ and $W^2$ affording the strongest signal varies depending on the kinds of $W^1$ and $W^2$. Therefore, $R^2$, $R^3$ and m are suitably selected by considering the kinds of $W^1$ and $W^2$ and the like.

The intramolecular distance between the two fluorescent groups is in the range of 10–100 Å, preferably 20–60 Å, more preferably about 30–50 Å. When the ring formed from $R^2$ and $R^3$ is a pyrrolidine ring, i.e., the residue is a proline residue, 20–60 Å corresponds to a proline stretch of about 5–16 residues, and 30–50 Å corresponds to 8–12 residues. The value of m is suitably such a number that the total amino acid residues containing the proline stretch should correspond to 20–60 Å, preferably 30–50 Å.

$W^1$ and $W^2$ each independently represent a fluorescent group. The fluorescent group used herein is a group having a property of giving fluorescence emission.

Preferred examples of the fluorescent group include fluorescein dyes, rhodamine dyes, 4,4-difluoro-4-bora-3a,4a-diaza-s-indacene dyes, cyanine dyes, phthalocyanine dyes, squalanine dyes and the like. Among these, those of fluorescein dyes, rhodamine dyes and 4,4-difluoro-4-bora-3a,4a-diaza-s-indacene dyes are preferred.

More specifically, there can be mentioned, for example, those derived from fluorescent dyes such as 5- or 6-carboxyfluorescein (abbreviated as FAM hereinafter), fluorescein, isothiocyanate, 5- or 6-carboxy-4',5'-dichloro-2',7'-dimethoxyfluorescein (abbreviated as JOE hereinafter), 5- or 6-carboxy-2',4',5',7'tetrachlorofluorescein, 5- or 6-carboxy-2', 4', 5', 7'tetrabromofluorescein, 5- or 6-carboxy-4,7-dichloro-2',7'-dimethoxyfluorescein, 5- or 6-carboxy-4,7,4',5'-tetrachloro-2',7'-dimethoxyfluorescein, 5- or 6-carboxy-2',7'-dimethoxyfluorescein, 5- or 6-carboxy-4,A7-dichloro-1',2',7',8'-dibenzofluorescein, 5- or 6-carboxy-4,7-dichloro-1',2',7',8'-dibenzofluorescein, 5- or 6-carboxytetramethylrhodamine (abbreviate as TMR hereinafter), 5- or 6-carboxyrhodamine X (abbreviated as XR hereinafter), 5- or 6-carboxyrhodamine 6G (abbreviated as R6G hereinafter), 5- or 6-carboxyrhodamine 110 (abbreviated as R110 hereinafter), 4,4-difluoro-1,3,5,7-tetramethyl-4-bora-3a,4a-diaza-s-indacene-8-propionic acid (abbreviated as BODIPY 493/503 hereinafter), 2,6-dibromo-4,4-difluoro-5,7-dimethyl-4-bora-3a,4a-diaza-s-indacene-8-propionic acid (abbreviated as BODIPY FL Br2 hereinafter), 4,4-difluoro-5-phenyl-4-bora-3a,4a-diaza-s-indacene-8-propionic acid (abbreviated as BODIPY R6G hereinafter), 4,4-difluoro-5,7-diphenyl-4-bora-3a,4a-diaza-s-indacene-8-propionic acid (abbreviated as BODIPY 530/550 hereinafter), 6-((4,4-difluoro-1,3-dimethyl-5-(4-methoxyphenyl)-4-bora-3a,4a-diaza-s-indacene-2-propionyl)amino)hexanoic acid (abbreviated as BODIPY TMR hereinafter), (Oregon Green 488)-carboxylic acid, ethidium bromide, 2-methoxy-6-chloro-9-aminoacridine, and 4-trifluoromethyl-7-ω-bromopropylaminocoumarin.

When the compounds of the present invention are used as a terminator, it can be emphasized that they are four kinds of energy transfer terminators which has been designed in order to more efficiently realize strong signal intensity in the method for DNA sequencing based on the chain terminator method compared with conventional four-color fluorescent terminators. In order to perform the termination reaction for the four kinds of bases, A, G, C and T, simultaneously four kinds of sets (combinations of the donor dye and the acceptor dye, occasionally they are collectively referred to as reporters) are provided.

When the compounds of the present invention are used, one of $W^1$ and $W^2$ serves as the donor dye, and the other serves as the acceptor dye. Specific preferred examples of the set of $W^1$ and $W^2$ include, but not limited to, sets of donor dye A (FAM), acceptor dye B (FAM, JOE, TMR, XR), donor dye A (FAM), acceptor dye B (FAM, R6G, TMR, XR), donor dye A (FAM), acceptor dye B (R6G, TMR, XR, R110), donor dye A (BODIPY 493/503), acceptor dye B (BODIPY FLBr2, BODIPY R6G, BODIPY TMR, BODIPY 530/550), donor dye A (FAM), acceptor dye B (BODIPY FLBr2, BODIPY R6G, BODIPY TMR, BODIPY 530/550), donor dye A (Oregon Green 488), acceptor dye B (BODIPY FLBr2, BODIPY R6G, BODIPY TMR, BODIPY 530/550) and the like.

The compounds of the present invention has the advantage that, when they are used as a terminator for example, they can be incorporated by an RNA polymerase or a DNA polymerase without steric hindrance because they are composed of two kinds of fluorescent dyes bound to one mono- or oligonucleotide. In addition, the compounds of the present invention have a chemical structure which is designed for quickly taking a specific higher structure for high sensitivity detection based on the principle of energy transfer, and therefore they are useful as a terminator, a primer and an initiator.

The compounds of the present invention represented by the above general formula (1) can be synthesized by, for example, reacting a compound represented by the following general formula (7) with a compound represented by the following general formula (8) according to the following reaction formula (V).

  (7)

In the formula, Q and V have the same meanings as defined above.

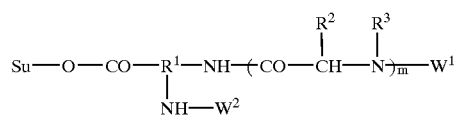

In the formula, Su represents a succinimide group, and the other symbols have the same meanings as defined above.

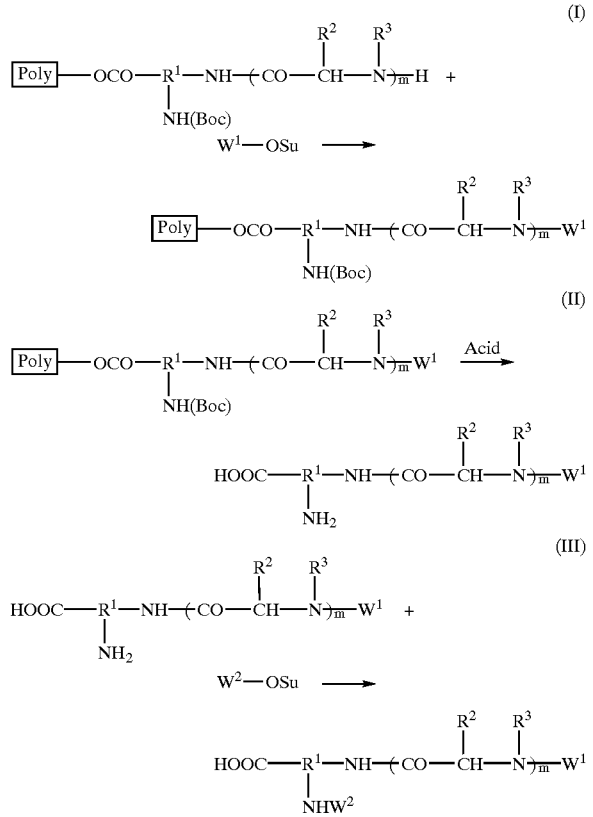

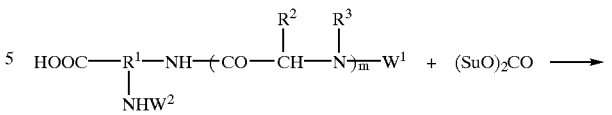

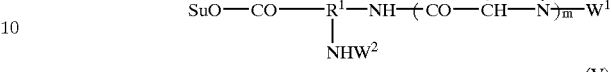

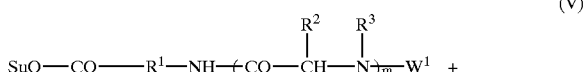

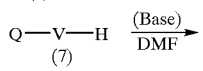

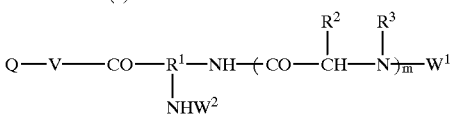

That is, as shown in the above reaction formula [V], a compound represented by the general formula (7) and a compound represented by the general formula (8) can be reacted in a solvent such as DMF and DMF/water in the presence of a basic catalyst such as 4-dimethylaminopyridine as required at 10–40° C. for 1 to several hours to afford a compound of the general formula (1).

The compounds represented by the general formula (7) can be synthesized by, for example, the method mentioned in Japanese Patent Unexamined Publication (KOKAI) No. Hei 10-158293/1998, columns 9–18 , [0056]–[0067], and specifically, by the method described in [Examples] thereof.

The compounds represented by the general formula (8) can be synthesized according to (I)–(IV) in the reaction scheme mentioned above. The symbol "Poly" in the reaction scheme represents a resin (solid phase). That is, for example, they can be readily obtained by, for example, introducing $W^1$ into the N-terminus of $(Pro)_{m-\epsilon}Boc\text{-}Lys$ wherein Pro represents a proline residue, Lys represents a lysine residue, Boc represents a t-butyloxycarbonyl group, and m represents a positive integer, which is synthesized by a conventional method such as the solid phase method [Reaction Formula (I)], then removing the Boc group [Reaction Formula (II)], introducing $W^2$ into the free amino group [Reaction Formula (III)], and introducing a succinimide group (Su) [Reaction Formula (IV)].

Nucleotide Sequence Determination Method
(1) Method Utilizing Terminator Having Energy Transfer Function The nucleotide sequence determination method of the present invention using a terminator having energy transfer function include the following methods:

a method for determining DNA sequences based on the chain terminator method, wherein the chain termination reaction is performed by using a terminator comprising a 3'-deoxyribonucleotide residue and two kinds of reporters that can be a donor and an acceptor of energy transfer, and an RNA polymerase (this method is referred to as the first method hereinafter), and a method for determining DNA sequences based on the chain terminator method, wherein the chain termination reaction is performed by utilizing a compound of the present invention represented by the general formula (1) as a terminator (this method is referred to as the second method hereinafter). The latter method includes a method utilizing a compound represented by the general formula (1) wherein Q is a 2',3'-dideoxyribonucleotide residue as a terminator and a DNA polymerase, and a method utilizing a compound represented by the general formula (1) wherein Q is a 3'-deoxyribonucleotide residue as a terminator and an RNA polymerase. The method using an RNA polymerase overlaps the above first method.

The first method mentioned above utilizes a terminator comprising a 3'-deoxyribonucleotide residue, and two kinds of reporters which can be a donor and an acceptor for energy transfer. The reporter may be, for example, a fluorescent group, and in addition, it can be selected from, for example, the group consisting of phosphorescent groups, spin-labeled groups and groups having high electron density. The two kinds of reporters on the terminator are preferably placed with a distance sufficient for causing energy transfer from the donor to the acceptor. The distance sufficient for causing energy transfer from the donor to the acceptor is, for example, in the range of 10–100 Å.

When the reporter comprises a fluorescent group, the fluorescent group can be suitably selected considering intensity and wavelength of fluorescence, easiness of incorporation by an RNA polymerase and the like. However, the fluorescent group should be a fluorescent group producing detectable luminescence emission subsequent to stimulation by energy absorption from a suitable source such as argon laser, and the fluorescent group is preferably used as a set in which an emission wavelength of one member resonates with an excitation wavelength of another member.

As preferred examples of the fluorescent group, those mentioned for $W^1$ and $W^2$ hereinbefore can be mentioned.

When the reporter comprises a fluorescent group, the intramolecular distance between the two fluorescent dyes (the donor and the acceptor) is designed to be constant. As a structure for obtaining such a constant intramolecular distance, for example, a stretch of proline can be mentioned as discussed above. The intramolecular distance between the two fluorescent groups is in the range of 10–100 Å, preferably 20–60 Å, more preferably about 30–50 Å. As for the proline stretch, 20–60 Å corresponds to about 5–16 residues, and 30–50 Å corresponds to 8–12 residues.

When the reporter comprises a fluorescent group, it is preferred to select four kinds of energy transfer terminators which are designed in the method for DNA sequencing based on the chain terminator method so as realize more efficiently stronger signal intensity compared with conventional four-color fluorescent terminators. In order to simultaneously perform the termination reactions for the four kinds of bases, A, G, C and T, four kinds of sets (combinations of the donor dye and the acceptor dye) are used. Preferred specific examples of the set include, but not limited to, sets of donor dye A (FAM), acceptor dye B (FAM, JOE, TMR, XR), donor dye A (FAM), acceptor dye B (FAM, R6G, TMR, XR), donor dye A (FAM), acceptor dye B (R6G, TMR, XR, R110), donor dye A (BODIPY 493/503), acceptor dye B (BODIPY FL Br2, BODIPY R6G, BODIPY TMR, BODIPY 530/550), donor dye A (FAM), acceptor dye B (BODIPY FL Br2, BODIPY R6G, BODIPY TMR, BODIPY 530/550), donor dye A (Oregon Green 488), acceptor dye B (BODIPY FL Br2, BODIPY R6G, BODIPY TMR, BODIPY 530/550) and the like.

As specific examples of the terminator where the reporter comprises a fluorescent group, the compounds of the present invention represented by the general formula (1) can be mentioned.

The second method for determining nucleotide sequences of the present invention is a method based on the chain terminator method, and characterized in that the chain termination reaction is performed by using a compound of the present invention represented with the general formula (1) as the terminator. Provided that the second method of the present invention includes a method utilizing a DNA polymerase as the polymerase in addition to a method utilizing an RNA polymerase as polymerase.

For the first method and the second method of the present invention, known methods can be utilized as they are except that the compounds mentioned above should be used as the terminator. For example, a method utilizing DNA polymerase as the polymerase is disclosed in Japanese Patent Unexamined Publication (KOKAI) No. Hei 1-180455/1989, International Patent Application Publication in Japanese (KOHYO) No. Hei 5-502371/1993, International Patent Application Publication in Japanese (KOHYO) No. Hei 6-510433/1994 and the like. The DNA polymerase may be a polymerase having improved heat resistance or a mutant polymerase of which difference of incorporation ratio depending on the kind of bases is improved.

When a DNA polymerase is used as the polymerase, and a compound of the general formula (1) is used as the terminator, this compound preferably has a 2',3'-dideoxyribonucleotide residue and n1 or n2 is preferably 3 or more, more preferably 3–10, because such a compound shows good incorporation by DNA polymerase, and affords highly precise sequence data.

When an RNA polymerase is used as the polymerase, a terminator of the present invention having 3'-deoxyribonucleotide residue or a compound of the present invention having 3'-deoxyribonucleotide residue represented by the general formula (1) is used as the terminator. As the method for determining nucleotide sequences using an RNA polymerase as the polymerase, for example, the method described in WO96/14434 can be used except that the terminator or the compound of the present invention is used.

That is, ribonucleoside 5'-triphosphates comprising ATP, GTP, CTP, and UTP or derivatives thereof and the terminators, deoxyribonucleoside i.e., one or more kinds, preferably four kinds of 3'-deoxyribonucleoside 5'-triphosphates (3'-dNTP derivatives) comprising derivatives of 3'-dATP, 3'-dGTP, 3'-dCTP, and 3'-dUTP selected from the terminators of the present invention, can be reacted in the presence of an RNA polymerase and DNA fragments containing a promoter sequence for the RNA polymerase to afford nucleic acid transcription products, the resulting nucleic acid transcription products can be separated, and DNA sequence can be determined by reading nucleic acid sequence from the obtained separated fractions.

The RNA polymerase may be a polymerase having improved heat resistance, or a mutant polymerase of which difference of incorporation ratio depending on the kind of bases is improved. The DNA fragment which will be used as a template is not particularly limited so long as it contains a promoter sequence for the RNA polymerase. For example, the DNA fragment containing a promoter sequence can be a DNA product amplified by polymerase chain reaction (PCR). Further, nucleic acid transcription reaction by the method of the present invention can be performed with such an amplified DNA product without removing therefrom the primers and/or 2'-deoxyribonucleoside 5'-triphosphates and/or the derivatives thereof used for the polymerase chain reaction. The DNA fragment containing a promoter sequence may also be a DNA fragment obtained by ligating the promoter sequence and a DNA fragment to be amplified followed by cloning in a suitable host cell.

When an RNA polymerase is used as the polymerase, and a compound of the general formula (1) is used as the terminator, this compound preferably has a 3'-deoxyribonucleotide residue, and n1 or n2 of the compound is preferably an integer of 4 or more, more preferably 4–10, because such a compound shows good incorporation by RNA polymerase, and affords highly precise sequence data.

In the DNA sequence determination method of the present invention, four kinds of terminators corresponding to four kinds of bases selected from the terminators of the present invention or the compounds represented by the above general formula (1) (each terminator has one of different four kinds of reporters as the acceptor) can be used, and the chain termination reactions can be performed in the same reaction system. When compounds represented by the general formula (1) are used as terminators, one of $W^1$ and $W^2$ serves as the acceptor, and each compound should have one of four different kinds of acceptors. In this method, a nucleotide sequence can be efficiently determined with a smaller number of operation step by performing the incorporation reaction of terminators corresponding to the four kinds of bases, A, G, C and T in a single tube.

Further, in the methods of the present invention, the chain termination reaction is preferably performed in the presence of inorganic pyrophosphatase as described hereinafter, because it can minimize. the difference of peak heights obtained corresponding to each ribonucleotide, and hence improve accuracy of the sequence reading.

(2) Method Utilizing Primer Having Energy Transfer Function

The third method for DNA sequence determination of the present invention is a method for determining DNA sequences based on the primer method, and characterized in that it utilizes a compound of the present invention represented by the general formula (1) where Q is an oligonucleotide residue, in particular, Q is an oligonucleotide residue having 2'-deoxyribonucleotide residue at its end as a primer.

For the third method of the present invention, known dideoxy methods utilizing a DNA polymerase can be used except that the compound mentioned above is used as the primer. As the known methods, for example, the methods disclosed in WO95/21266, Japanese Patent Unexamined Publication (KOKAI) No. Hei 10-88124/1998 and the like can be utilized.

(3) Method Utilizing Initiator Having Energy Transfer Function

The fourth method for DNA sequence determination of the present invention is a method for determining DNA sequences based on the chain terminator method, and characterized in that the chain termination reaction is performed by using an initiator comprising a mono- or oligonucleotide residue not having a phosphate group, or having a mono- or diphosphate residue at the 5' end and two kinds of reporters that can be a donor and an acceptor of energy transfer, and an RNA polymerase. As the above initiator, a compound of the present invention represented by the general formula (1) where Q is a mono- or oligonucleotide residue not having a phosphate group, or having a mono- or diphosphate residue at the 5' end can be used.

More specifically, this method is a method for determining DNA sequences where ribonucleoside 5'-triphosphates comprising ATP, GTP, CTP, and UTP or derivatives thereof and one kind of 3'-deoxyribonucleoside 5'-triphosphate (referred to as 3'-dNTP derivative hereinafter) selected form the group consisting of 3'-dATP, 3'-dGTP, 3'-dCTP, 3'-dUTP and derivatives thereof are reacted in the presence of an RNA polymerase and DNA fragments containing a promoter sequence for the RNA polymerase to afford nucleic acid transcription products, the resulting nucleic acid transcription products are separated, and DNA sequence is determined by reading nucleic acid sequence from the obtained separated fractions, and it utilizes the initiator mentioned above as the initiator for the nucleic acid transcription reaction. The 3'-dNTP derivatives as the terminators can be unlabeled compounds.

Principles of the method for enzymatically synthesizing nucleic acid transcription products by using an RNA polymerase and a DNA fragment containing a promoter sequence for the RNA polymerase as a template, the method for separating the transcription products, and the method for reading nucleic acid sequence from the separated fractions are known in the art. Accordingly, for these methods, any known methods, conditions, apparatuses and the like can be used according to circumstances. For example, one can refer to the descriptions of WO96/14434 concerning the terminator method.

The DNA fragment which will be used as a template is not particularly limited so long as it contains a promoter sequence for the RNA polymerase. For example, the DNA fragment containing a promoter sequence can be a DNA product amplified by polymerase chain reaction. Further, the nucleic acid transcription reaction by the method of the present invention can be performed with such an amplified DNA product without removing therefrom the primers and/or 2'-deoxyribonucleoside 5'-triphosphates and/or the derivatives thereof used for PCR. The DNA fragment containing a promoter sequence may also be a DNA fragment obtained by ligating the promoter sequence and a DNA fragment to be amplified and cloned in a suitable host cell. That is, the DNA sequence to be amplified, primers, conditions for the amplification and the like used in the present invention are not particularly limited.

For example, the reaction system of the polymerase chain reaction for amplification of a DNA fragment containing a promoter sequence may contain 10–50 ng of genomic DNA or 1 pg of cloned DNA, 10 $\mu$M of each primer, and 200 $\mu$M of each 2'-deoxyribonucleoside 5'-triphosphate (dATP, dGTP, dCTP, dTTP) in 20 $\mu$l volume, and the reaction can be performed using Taq polymerase as the DNA polymerase in such a reaction system.

However, either one of the primers for the polymerase chain reaction or the amplified inserted DNA (insert) should contain a promoter sequence for An RNA polymerase mentioned hereinafter. In the direct transcriptional sequencing method, by using two kinds of primers, one of which has a phage promoter sequence, or amplified inserted DNA containing a phage promoter sequence, the resulting PCR products can be subjected to in vitro transcription by an RNA polymerase functioning with such a promoter.

The promoter sequence for an RNA polymerase can be suitably selected according to the kind of an RNA polymerase to be used.

In the fourth method of the present invention, transcripts of RNA and the like are synthesized from a DNA fragment containing a promoter sequence. Because the DNA fragment contains the promoter sequence for an RNA polymerase, this promoter sequence is recognized by the above-mentioned RNA polymerase, and nucleic acid transcripts such as RNA transcripts are synthesized.

In the synthesis of transcripts of RNA and the like, ribonucleoside 5'-triphosphate (NTP) comprising ATP, GTP, CTP and UTP or derivatives thereof and one kind of 3'-dNTP derivative are reacted in the presence of the nucleic acid transcription initiator and an RNA polymerase. Further, the term 3'-dNTP derivative is used herein to collectively refer to 3'-dATP, 3'-dGTP, 3'-dCTP, 3'-dUTP and derivative thereof. As the ribonucleoside 5'-triphosphates (NTPs), at least four kinds of compounds having different bases, some of which may be derivatives of NTP, are necessary for the synthesis of transcripts.

The 3'-dNTP derivatives are incorporated at the 3' ends of transcriptional products, RNA or nucleic acid, thereby 3'-hydroxy groups no longer exist to inhibit the synthesis of RNA or nucleic acid. As a result, RNA or nucleic acid fragments with various lengths having the 3'-dNTP derivatives at the 3' end are provided. Such ribonucleoside analogues are obtained for each of the four kinds of 3'-dNTP derivatives with different bases. The provided four kinds of ribonucleoside analogues can be used for the sequencing of RNA or nucleic acid [Vladimir D. Axelred et al. (1985) Biochemistry Vol. 24, 5716–5723].

One kind of the 3'-dNTP derivatives is used for one nucleic acid transcription reaction, and the nucleic acid transcription reaction is performed four times by using each of different four kinds of the 3'-dNTP derivatives to afford four kinds of transcription products with different bases of the 3'-dNTP derivatives at the 3' end. In one nucleic acid transcription reaction, a transcription product which is a mixture of various kinds of RNA or nucleic acid fragments with the same 3'-dNTP derivative at the 3' end and different molecular weight is obtained. The obtained four kinds of transcription products can be independently separated and used for sequencing described hereinafter. Alternatively, two or more of the four kinds of the transcription products can be mixed, and the resulting mixture can be subjected to separation and used for sequence reading.

The RNA polymerase used in the fourth method of the present invention may be either a wild type RNA polymerase or a mutant RNA polymerase. As for the RNA polymerase, one can refer to the descriptions for the first and the second methods hereinbefore.

Inorganic Pyrophosphatase

In the first to fourth methods of the present invention, the nucleic acid transcription reaction is preferably performed in the presence of an inorganic pyrophosphatase. This makes it possible to minimize the difference of peak heights (strength of signal) of the labeled ribonucleotides, thereby accuracy of the sequence reading can be improved and more accurate sequence data can be afforded.

Pyrophosphorolysis is caused by increase of pyrophosphate produced by the DNA synthesis, and act to promote the reaction in such a manner that the synthesized DNA products should be decomposed. As a result, the pyrophosphorolysis will inhibit the sequencing in the dideoxy sequencing method utilizing a DNA polymerase. On the other hand, it has been known that, when an inorganic pyrophosphatase is used in the dideoxy sequencing method which uses a DNA polymerase, it inhibits the pyrophosphorolysis and thus afford stable sequence data [Japanese Patent Unexamined Publication (KOHYO) No. Hei 4-506002/1992].

Pyrophosphorolysis is also effective in the sequencing method which uses an RNA polymerase. That is, by performing the nucleic acid transcription reaction in the presence of an inorganic pyrophosphatase, it becomes possible to minimize the difference of peak heights (strength of signal) of the labeled ribonucleotides, thereby more stable sequence data can be afforded.

The inorganic pyrophosphatase (EC.3.6.1.1) can be obtained as a commercially available product, and, for example, it is marketed as INORGANIC PYROPHOSPHATASE by Sigma, and as Pyrophosphatase by Boehringer. While the amount of the inorganic pyrophosphatase to be used depends on the degree of activities of the inorganic pyrophosphatase and an RNA polymerase, it can be suitably used, for example, in an amount of $10^{-6}$ to $10^{-2}$ units per unit of the RNA polymerase.

According to the present invention, five-twentyfold higher sensitivity for the signals can be obtained with the same number of molecules compared with that obtained by using conventional fluorescence-labeled terminators having only one reporter such as a fluorescent dye. It is particularly effective when using multiple capillary sequencer and the like, or when conducting electrophoresis using lithography channels or ultrafine lithography channels. In particular, use of an increased number of lanes (capillaries) tends to require decreased sectional area of the electrophoresis lanes, and it is considered that amount of DNA that can be loaded is substantially proportional to the sectional area.

Therefore, the amount of DNA that can be loaded is considered to be in inverse proportion to square of electrophoresis lane diameter, and the width of the ultrafine electrophoresis channels of capillary array or lithography which is used for multiple lanes is in proportion to the diameter of one capillary. Eventually, if the width of the whole capillary array is constant, sensitivity increased in proportion to square number of the capillaries is required.

It is considered that the present invention is extremely effective for such use of multiple sequencing lanes. According to the present invention, because structures having an extremely large molecular weight are bonded to one terminator nucleotide, mobility of the final sequencing products in electrophoresis tends to be slower compared with that observed with conventional terminators. Therefore, it is suitable to newly program a computer software for base call of sequencer.

EXAMPLE

The present invention will be further explained more in detail with reference to the following examples.

The abbreviations used in the following examples are as follows.

Fmoc: a 9-fluorenylmethyloxycarbonyl group

Boc: a t-butyloxycarbonyl group

Lys: lysine

Pro: proline

Ac: an acetyl group

SYNTHESIS EXAMPLE 1

Synthesis of FAM-(Pro)8-Lys(εTMR)

(1) Synthesis of FAM-(Pro)8-Lys

Starting from αFmoc-εBoc-Lys-Alko resin (100–200 mesh, Watanabe Chemical Industry, 5.0 g, 2.4 mmol as αFmoc-εBoc-Lys), the title compound was synthesized by the solid phase method according to the method described in literature ("Fundamentals and Experiments of Peptide Synthesis", Maruzen Shuppan, p.218).

That is, αFmoc-εBoc-Lys-Alko resin was first treated with piperidine to remove the Fmoc group. To a solution of the resulting resin and threefold amount of Fmoc-Pro (Wako Pure Chemical Industries Ltd.) in equivalence as to Lys on the resin in 1-methyl-2-pyrrolidone, threefold amount in equivalence of HOBt and threefold amount in equivalence of N,N'-diisopropylcarbodiimide were added, and condensation reaction was performed at room temperature for five hours to successively introduce amino acids. After all of the amino acids were incorporated, threefold amount in equivalence of 5-carboxyfluorescein succinimide ester (Molecular Probe) was condensed. After the reaction was completed, the resin was washed with MeOH, added with a mixture (100 ml) of 55% TFA-dichloromethane and anisole (1 ml), and allowed to react at room temperature for one hour with stirring to cleave the desired FAM-labeled polypeptide from the resin and simultaneously remove the Boc group (the protecting group of $\epsilon$-amino group of Lys). After the reaction was completed, the resin was removed by filtration, and the filtrate was concentrated under reduced pressure, and added with ether to precipitate the reaction product. The precipitates were collected, and dried in a desiccator to afford 2.2 g of FAM-(Pro)8-Lys. (2) Synthesis of FAM-(Pro)8-Lys($\epsilon$TMR)

500 mg of the FAM-(Pro)8-Lys synthesized in Synthesis Example 1-(1) was dissolved in DMF (1 ml), added with threefold amount in equivalence of triethylamine and 2.5-fold amount in equivalence of 5-carboxytetramethylrhodamine succinimide ester (Molecular Probe), and allowed to react at room temperature for 19 hours. After the reaction was completed, the reaction mixture was concentrated under reduced pressure, and the resulting residue was purified by using a gel filtration column (Sephadex LH20, Pharmacia) to afford FAM-(Pro)8-Lys($\epsilon$TMR) (420 mg).

SYNTHESIS EXAMPLE 2

Synthesis of FAM-(Pro)8-Lys($\epsilon$XR)

From the FAM-(Pro)8-Lys obtained in Synthesis Example 1-(1) (500 mg) and 2.5-fold amount in equivalence of 5-carboxy-X-rhodamine succinimide ester (Molecular Probe), FAM-(Pro)8-Lys($\epsilon$XR) (380 mg) was obtained by using the same reagents and the same procedure as in Synthesis Example 1-(2).

SYNTHESIS EXAMPLE 3

Synthesis of FAM-(Pro)8-Lys($\epsilon$R6G)

From the FAM-(Pro)8-Lys obtained in Synthesis Example 1-(1) (500 mg) and 2.5-fold amount in equivalence of 5-carboxyrhodamine 6G succinimide ester (Molecular Probe), FAM-(Pro)8-Lys($\epsilon$R6G) (400 mg) was obtained by using the same reagents and performing the same procedure as in Synthesis Example 1-(2).

SYNTHESIS EXAMPLE 4

Synthesis of FAM-(Pro)8-Lys($\epsilon$R110)

From the FAM-(Pro)8-Lys obtained in Synthesis Example 1-(1) (500 mg) and 3.5-fold amount in equivalence of 5-carboxyrhodamine-110-bistrifluoroacetate succinimide ester (Molecular Probe), FAM-(Pro)8-Lys($\epsilon$R110) (300 mg) was obtained by using the same reagents and performing the same procedure as Synthesis Example 1-(2) after the reaction was completed.

SYNTHESIS EXAMPLE 5

Synthesis of FAM-(Pro)10-Lys($\epsilon$TMR)

(1) Synthesis of FAM-(Pro)10-Lys

Starting from $\alpha$Fmoc-$\epsilon$Boc-Lys-Alko resin (100–200 mesh, Watanabe Chemical Industry, 5.0 g, 2.4 mmol as $\epsilon$Fmoc- $\epsilon$Boc-Lys), H-Pro10-Lys(Boc)-Alko resin was synthesized in a manner similar to that of Synthesis Example 1(obtained amount: 6.8 g). The dried resin (1 g) was condensed with 5-carboxyfluorescein succinimide ester prepared from 5-carboxyfluorescein (Molecular Probe, 0.6 g), N-hydroxysuccinimide (0.37 g) and diisopropylcarbodiimide (500 $\mu$l).

After the reaction was completed, the resin was washed with DMF and MeOH, added with a mixture of 95% TFA and anisole 8 ml), and allowed to react at room temperature for one hour with stirring to cleave the desired FAM-labeled polypeptide from the resin. After the reaction was completed, the resin was removed by filtration, and the filtrate was concentrated under reduced pressure, and added with ether to precipitate the reaction product. The precipitates were collected, and dried in a desiccator to afford FAM-(Pro)10-Lys (0.63 g).

(2) Synthesis of FAM-(Pro)10-Lys($\epsilon$TMR)

The FAM-(Pro)10-Lys synthesized in Synthesis Example 5-(1) (13.7 mg) was dissolved in DMF (1 ml), added with triethylamine (20 $\mu$l) and 6-carboxytetramethylrhodamine succinimide ester (Molecular Probe, 4.88 mg), and allowed to react at room temperature for 19 hours. After the reaction was completed, the reaction mixture was concentrated under reduced pressure, and the resulting residue was purified by using a gel filtration column (Sephadex LH20, Pharmacia) to afford FAM-(Pro)10-Lys($\epsilon$TMR) (10.9 mg).

SYNTHESIS EXAMPLE 6

Synthesis of FAM-(Pro)10-Lys($\epsilon$XR)

The FAM-(Pro)10-Lys obtained in Synthesis Example 5-(1) (9.63 mg) was dissolved in DMF (1 ml), and added with triethylamine (20 $\mu$l) and 6-carboxy-X-rhodamine succinimide ester (Molecular Probe, 3.78 mg). Condensation reaction and purification were performed in the same manner as in Synthesis Example 5-(2) to afford FAM-(Pro)10-Lys($\epsilon$XR) (6.53 mg).

SYNTHESIS EXAMPLE 7

Synthesis of FAM-(Pro)10-Lys($\epsilon$R6G)

The FAM-(Pro)10-Lys obtained in Synthesis Example 5-(1) (3.18 mg) was dissolved in DMF (0.5 ml), and added with triethylamine (10 $\mu$l) and 6-carboxyrhodamine 6G succinimide ester (Molecular Probe, 1.11 mg). Condensation reaction and purification were performed in the same manner as in Synthesis Example 5-(2) to afford FAM-(Pro)10-Lys($\epsilon$R6G) (2.66 mg).

SYNTHESIS EXAMPLE 8

Synthesis of FAM-(Pro)10-Lys($\epsilon$R110)

The FAM-(Pro)10-Lys obtained in Synthesis Example 5-(1) (5.00 mg) was dissolved in DMF (0.5 ml), and added with triethylamine (10 $\mu$l ) and 5-carboxyrhodamine-110-bis-trifluoroacetate succinimide ester (Molecular Probe, 2.07 mg). Condensation reaction and purification were performed in the same manner as in Synthesis Example 5-(2) to afford FAM-(Pro)10-Lys($\epsilon$R110) (3.00 mg).

SYNTHESIS EXAMPLE 9

Synthesis of FAM-(Pro)12-Lys($\epsilon$TMR)

(1) Synthesis of FAM-(Pro)12-Lys Starting from $\alpha$Fmoc-$\epsilon$Boc-Lys-Alko resin (100–200 mesh, Watanabe Chemical Industry, 5.0 g, 2.4 nmol as αFmoc- εBoc-Lys), H-Pro12-Lys (Boc)-Alko resin was synthesized in a manner similar to that of Synthesis Example 1 (obtained amount: 7.2 g). The dried resin (1 g) was condensed with 5-carboxyfluorescein succinimide ester prepared from 5-carboxyfluorescein (Molecular Probe, 0.47 g), N-hydroxysuccinimide (0.27 g) and diisopropylcarbodiimide (330 µl).

After the reaction was completed, the resin was washed with DMF and MeOH, added with a mixture of 95% TFA and anisole (8 ml), and allowed to react at room temperature for one hour with stirring to cleave the desired FAM-labeled polypeptide from the resin. After the reaction was completed, the resin was removed by filtration, and the filtrate was concentrated under reduced pressure, and added with ether to precipitate the reaction product. The precipitates were collected, and dried in a desiccator to afford FAM-(Pro)12-Lys (0.58 g).

(2) Synthesis of FAM-(Pro)12-Lys(εTMR)

The FAM-(Pro)12-Lys (14.7 mg) synthesized in Synthesis Example 9-(1) was dissolved in DMF (1 ml), added with triethylamine (20 µl) and 6-carboxytetramethylrhodamine succinimide ester (Molecular Probe, 4.17 mg), and allowed to react at room temperature for 19 hours. After the reaction was completed, the reaction mixture was concentrated under reduced pressure, and the resulting residue was purified by using a gel filtration column (Sephadex LH20, Pharmacia) to afford FAM-(Pro)12-Lys(εTMR) (7.6 mg).

SYNTHESIS EXAMPLE 10

Synthesis of FAM-(Pro)12-Lys(εXR)

The FAM-(Pro)12-Lys obtained in Synthesis Example 9-(1) (3.76 mg) was dissolved in DMF (0.5 ml), and added with triethylamine (10 µl) and 6-carboxy-X-rhodamine succinimide ester (Molecular Probe, 1.33 mg). Condensation reaction and purification were performed in the same manner as in Synthesis Example 9-(2) to afford FAM-(Pro)12-Lys(εXR) (6.53mg).

SYNTHESIS EXAMPLE 11

Synthesis of FAM-(Pro)12-Lys(εR6G)

The FAM-(Pro)12-Lys obtained in Synthesis Example 9-(1) (3.18 mg) was dissolved in DMF (0.5 ml), and added with triethylamine (10 µl) and 6-carboxyrhodamine 6G succinimide ester (Molecular Probe, 1.11 mg). Condensation reaction and purification were performed in the same manner as in Synthesis Example 9-(2) to afford FAM-(Pro)12-Lys(εR6G) (2.75 mg).

SYNTHESIS EXAMPLE 12

Synthesis of FAM-(Pro)12-Lys(εR110)

The FAM-(Pro)12-Lys obtained in Synthesis Example 9-(1) (5.00 mg) was dissolved in DMF (0.5 ml), and added with triethylamine (10 µl) and 5-carboxyrhodamine-110-bis-trif luoroacetate succinimide ester (Molecular Probe, 0.86 mg). Condensation reaction and purification were performed in the same manner as in Synthesis Example 9-(2) to afford FAM-(Pro)12-Lys(εR110) (1.2 mg).

SYNTHESIS EXAMPLE 13

Synthesis of FAM-(Pro)4-Lys(εTMR)
(1) Synthesis of FAM-(Pro)4-Lys

Starting from αFmoc-εBoc-Lys-Alko resin (100–200 mesh, Watanabe Chemical Industry, 5.0 g, 2.4 mmol as αFmoc-εBoc-Lys), H-Pro4-Lys(Boc)-Alko resin was synthesized in a manner similar to that of Synthesis Example 1 (obtained amount: 5.4 g). The dried resin (400 mg) was condensed with 5-carboxyfluorescein succinimide ester prepared from 5-carboxyfluorescein (Molecular Probe, 256 mg) N-hydroxysuccinimide (72 g) and diisopropylcarbodiimide (90 µl). After the reaction was completed, the resin was washed with DMF and MeOH, added with a mixture of 95% TFA and anisole (8 ml), and allowed to react at room temperature for one hour with stirring to cleave the desired FAM-labeled polypeptide from the resin. After the reaction was completed, the resin was removed by filtration, and the filtrate was concentrated under reduced pressure, and added with ether to precipitate the reaction product. The precipitates were collected, and dried in a desiccator to afford FAM-(Pro)4-Lys (66.8 mg).

(2) Synthesis of FAM-(Pro)4-Lys(εTMR)

The FAM-(Pro)4-Lys (10 mg) synthesized in (1) was dissolved in DMF (1 ml), added with triethylamine (20 µl) and 6-carboxytetramethylrhodamine succinimide ester (Molecular Probe, 5.28 mg), and allowed to react at room temperature for 19 hours. After the reaction was completed, the reaction mixture was concentrated under reduced pressure, and the resulting residue was purified by using a gel filtration column (Sephadex LH20, Pharmacia) to afford FAM-(Pro)4-Lys(εTMR) (9.8 mg).

SYNTHESIS EXAMPLE 14

Synthesis of FAM-(Pro)6-Lys(εTMR)
(1) Synthesis of FAM-(Pro)6-Lys

Starting from αFmoc-εBoc-Lys-Alko resin (100–200 mesh, Watanabe Chemical Industry, 5.0 g, 2.4 mmol as αFmoc- εBoc-Lys), H-Pro4-Lys(Boc)-Alko resin was synthesized in amanner similar to that of Synthesis Example 1 (obtained amount: 5.8 g). The dried resin (218 mg) was condensed with 5-carboxyfluorescein succinimide ester prepared from 5-carboxyfluorescein (Molecular Probe, 128 mg), N-hydroxysuccinimide (73.7 mg) and diisopropylcarbodiimide (90 µl). After the reaction was completed, the resin was washed with DMF and MeOH, added with a mixture of 95% TFA and anisole (8 ml), and allowed to react at room temperature for one hour with stirring to cleave the desired FAM-labeled polypeptide from the resin. After the reaction was completed, the resin was removed by filtration, and the filtrate was concentrated under reduced pressure, and added with ether to precipitate the reaction product. The precipitates were collected, and dried in a desiccator to afford FAM-(Pro)6-Lys (20.6 mg).

(2) Synthesis of FAM-(Pro)6-Lys(εTMR)

The FAM-(Pro)6-Lys (12 mg) synthesized in (1) was dissolved in DMF (1 ml), added with triethylamine (20 µl) and 6-carboxytetramethylrhodamine succinimide ester (Molecular Probe, 5.5 mg), and allowed to react at room temperature for 19 hours. After the reaction was completed, the reaction mixture was concentrated under reduced pressure, and the resulting residue was purified by using a gel filtration column (Sephadex LH20, Pharmacia) to afford FAM-(Pro)6-Lys(εTMR) (9.29 mg).

REFERENCE EXAMPLE 1

Synthesis of Ac-(Pro)10-Lys(εTMR)
(1) Synthesis of Ac-(Pro)10-Lys

The H-Pro10-Lys(Boc)-Alko resin obtained in Synthesis Example 5-(1) (1.5 g) was swelled with DMF (35 ml), added with acetic anhydride (230 µl) and triethylamine (336 µl), and allowed to react for 20 hours. After the reaction was completed, the resin was washed with DMF and MeOH, added with a mixture of 95% TFA and anisole (8 ml), and allowed to react at room temperature for one hour with stirring to cleave the desired FAM-labeled polypeptide from the resin. After the reaction was completed, the resin was removed by filtration, and the filtrate was concentrated under reduced pressure, and added with ether to precipitate the reaction product. The precipitates were collected, and dried in a desiccator to afford Ac-(Pro)10-Lys (0.45 g).

(2) Synthesis of Ac-(Pro)10-Lys(εTMR)

The Ac-(Pro)10-Lys synthesized in Reference Example 1-(1) (11.8 mg) was dissolved in DMF (1 ml), added with triethylamine (20 µl) and 6-carboxytetramethylrhodamine succinimide ester (Molecular Probe, 5.7 mg), and allowed to react at room temperature for 19 hours. After the reaction was completed, the reaction mixture was concentrated under reduced pressure, and the resulting residue was purified by using a gel filtration column (Sephadex LH20, Pharmacia) to afford Ac-(Pro)10-Lys(εTMR) (6.0 mg).

REFERENCE EXAMPLE 2

Synthesis of Ac-(Pro)10-Lys (εXR)

The Ac-(Pro)10-Lys obtained in Reference Example 1-(1) (10 mg) was dissolved in DMF (1 ml), and added with triethylamine (20 µl) and 6-carboxy-X-rhodamine succinimide ester (Molecular Probe, 6.5 mg). Condensation reaction and purification were performed in the same manner as in Reference Example 1-(2) to afford Ac-(Pro)10-Lys(εXR) (4.2 mg).

REFERENCE EXAMPLE 3

Synthesis of Ac-(Pro)10-Lys(εR6G)

The Ac-(Pro)10-Lys obtained in Reference Example 1-(1) (10 mg) was dissolved in DMF (1 ml), and added with triethylamine (20 µl) and 6-carboxyrhodamine 6G succinimide ester (Molecular Probe, 5.3 mg). Condensation reaction and purification were performed in the same manner as in Reference Example 1-(2) to afford Ac-(Pro)10-Lys (εR6G) (2.66 mg).

REFERENCE EXAMPLE 4

Synthesis of Ac-(Pro)10-Lys(εR110)

The Ac-(Pro)10-Lys obtained in Reference Example 1-(1) (10.4 mg) was dissolved in DMF (1 ml), and added with triethylamine (20 µl) and 5-carboxyrhodamine-110-bis-trifluoroacetate succinimide ester (Molecular Probe, 8.3 mg). Condensation reaction and purification were performed in the same manner as in Reference Example 1-(2) to afford Ac-(Pro)10-Lys(εR110) (4.8 mg).

EXPERIMENTAL EXAMPLE 1

The energy transfer dyes which were compounds having 10 proline residues [FAM-(Pro)10-Lys(εTMR) FAM-(Pro)10-Lys (εXR),FAM-(Pro)10-Lys(εR6G), FAM-(Pro)10-Lys (εR110)], and the compounds having 10 proline residues and a single dye [Ac-(Pro)10-Lys(εTMR), Ac-(Pro)10-Lys (εXR), Ac-(Pro)10-Lys (εR6G), Ac-(Pro)10-Lys(εR110)] were compared for fluorescence emission intensity in 40 mM Tris-hydrochloric acid buffer (pH 8.0).

Each dye solution was excited at an excitation wavelength of 488 nm, and the fluorescence emission was measured at a wavelength of 580 nm (TMR), 610 nm (XR), 560 nm (R6G), or 530 nm (R110) using Hitachi F-4010 type spectrophotofluorometer. The obtained relative intensities of the dyes were shown in FIG. 6 as a bar graph.

Figure 6:
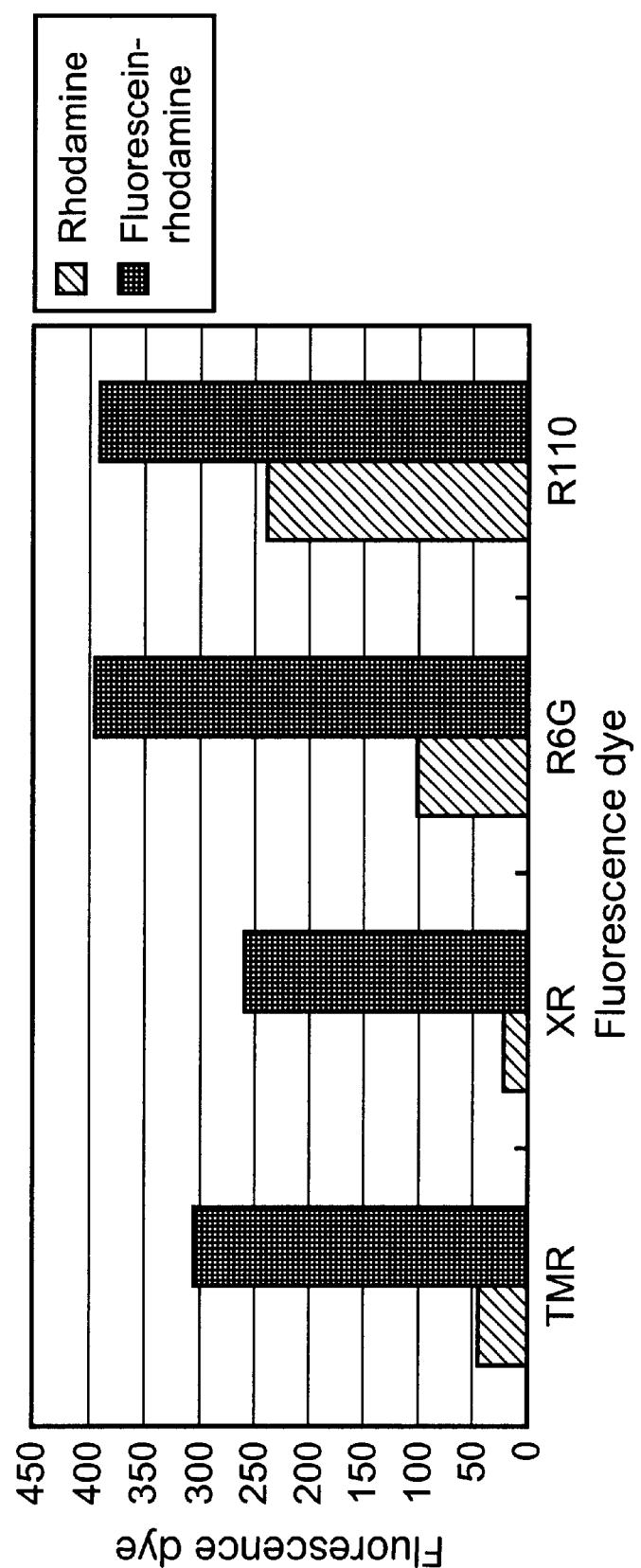
FIG. 6 shows comparison of fluorescence intensity of energy transfer dyes provided in Experimental Example 1.

As seen from FIG. 6, the energy transfer dyes exhibited markedly stronger fluorescence compared with the acceptor dyes themselves.

EXAMPLE 1

Synthesis of FAM- and TMR-labeled 3'-Deoxyuridine-5'-triphosphate (FAM- and TMR-labeled 3'-dUTP) (Compound 10)

To a solution of the FAM-(Pro)8-Lys(εTMR) obtained in Synthesis Example 1 (54.1 mg) in DMF (1 ml), N,N'-disuccinimidyl carbonate (8.2 mg) and 4-dimethylaminopyridine (3.9 mg) were added under nitrogen gas flow, and allowed to react at room temperature for two hours. The reaction mixture was added to a mixture of DMF/water containing 5-(6"-amino-1"-hexynyl)-3'-deoxyuridine-5'-triphosphate (8 µmol), and stirred at room temperature overnight. The reaction mixture was diluted with water (30 ml), and purified by DEAE-Toyopearl ion exchange column chromatography (1.7×15 cm, eluent; triethylammonium hydrogencarbonate buffer containing 40% acetonitrile (pH 7.5), 0.1 M→0.7 M linear gradient, total volume; 2 L).

EXAMPLE 2

Synthesis of FAM- and XR-labeled 3'-deoxycytidine-5'-triphosphate (FAM- and XR-labeled 3'-dCTP) (Compound 11)

To a solution of the FAM-(Pro)8-Lys(εXR) obtained in Synthesis Example 2 (71.9 mg) in DMF (1 ml), N,N'-disuccinimidyl carbonate (10.2 mg) and 4-dimethylaminopyridine (4.9 mg) were added under nitrogen gas flow, and allowed to react at room temperature for two hours. The reaction mixture was added to a mixture of DMF/water containing 5-(6"-amino-1"-hexynyl)-3'-deoxycytidine-5'-triphosphate (10 µmol), and stirred at room temperature for overnight. The product was purified in a manner similar to that of Example 1.

EXAMPLE 3

Synthesis of FAM- and R6G-labeled 3'-Deoxyadenosine-5'-triphosphate (FAM- and R6G-labeled 3'-dATP) (Compound 12)

To a solution of the FAM-(Pro)8-Lys(εR6G) obtained in Synthesis Example 3 (55.1 mg) in DMF (1 ml), N,N'-disuccinimidyl carbonate (8.2 mg) and 4-dimethylaminopyridine (3.9 mg) were added under nitrogen gas flow, and allowed to react at room temperature for two hours. The reaction mixture was added to a mixture of DMF/water containing 5-(6"-amino-1"-hexynyl)-3'-deoxyadenosine-5'-triphosphate (8 µmol), and stirred at room temperature overnight. The product was purified in a manner similar to that of Example 1.

EXAMPLE 4

Synthesis of FAM- and R110-labeled 3'-deoxyguanosine-5'-triphosphate (FAM- and R110-labeled 3'-dGTP) (Compound 13)

To a solution of the FAM-(Pro)8-Lys(εR110) obtained in Synthesis Example 4 (52.4 mg) in DMF (1 ml), N,N'-disuccinimidyl carbonate (8.2 mg) and 4-dimethylaminopyridine (3.9 mg) were added under nitrogen gas flow, and allowed to react at room temperature for two hours. The reaction mixture was added to a mixture of DMF/water containing 5-(6"-amino-1"-hexynyl)-3'-deoxyguanosine-5'-triphosphate (8 μmol), and stirred at room temperature overnight. The product was purified in a manner similar to that of Example 1.

The structural formulae of Compounds 10–13 obtained in Examples 1–4 are shown below.

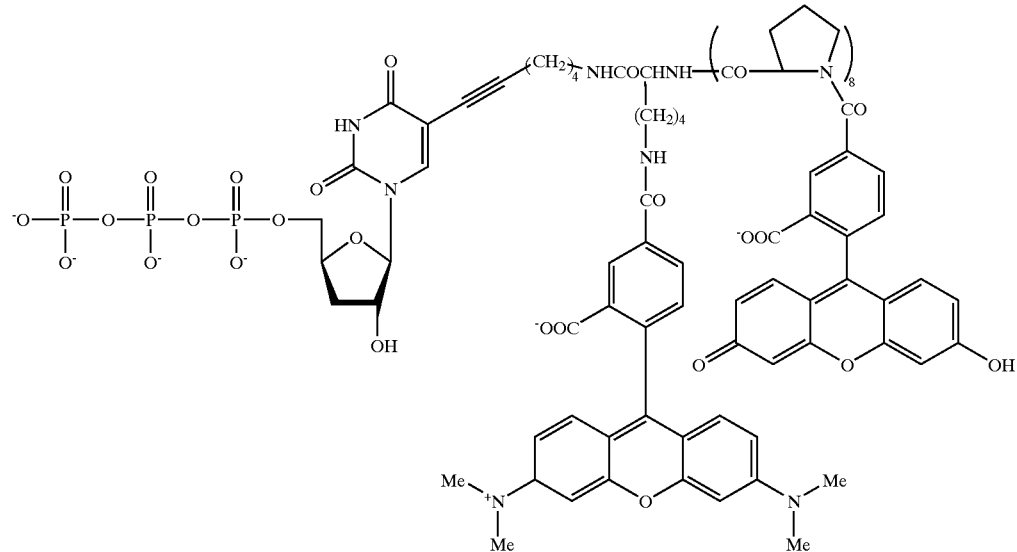

(10)

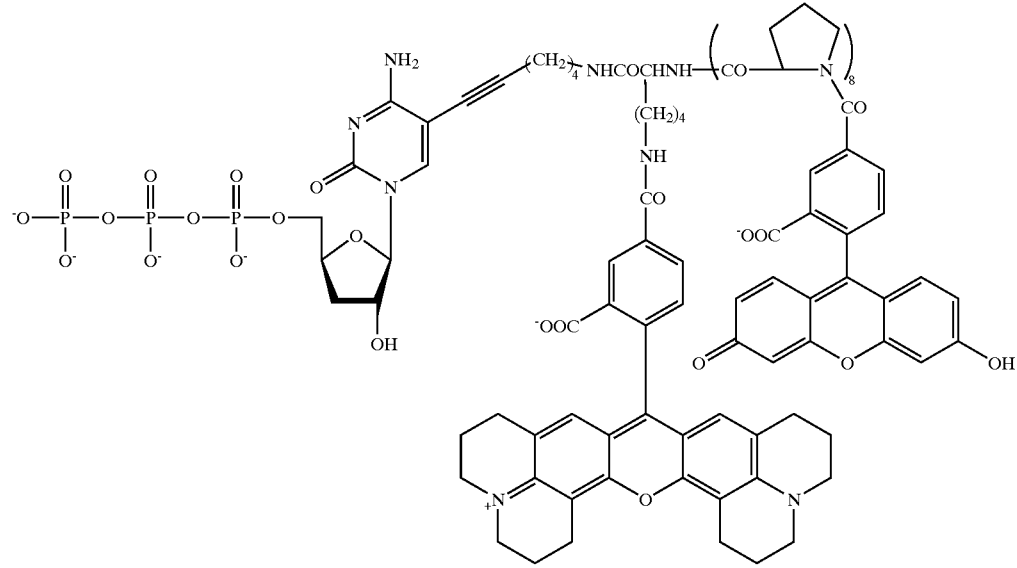

(11)

(12)

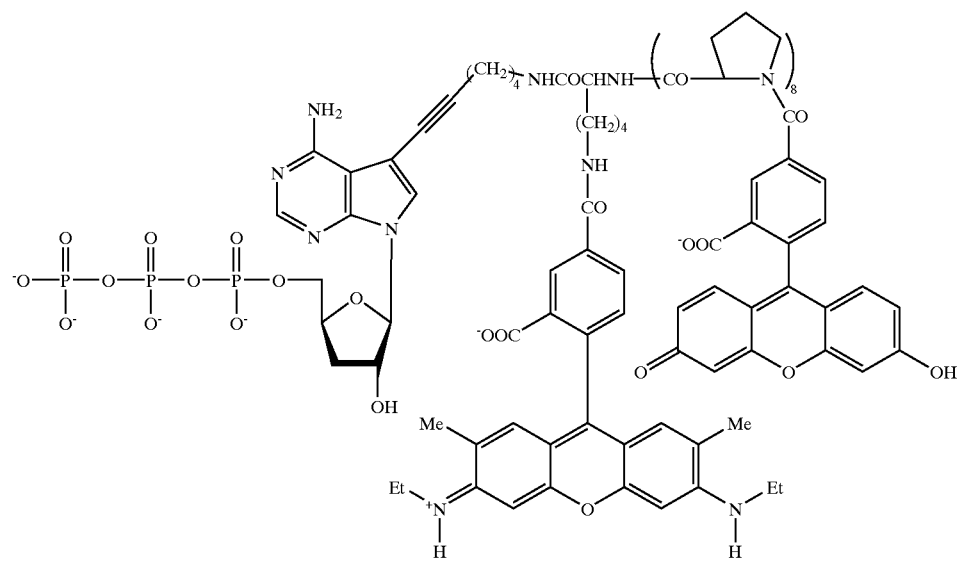

(13)

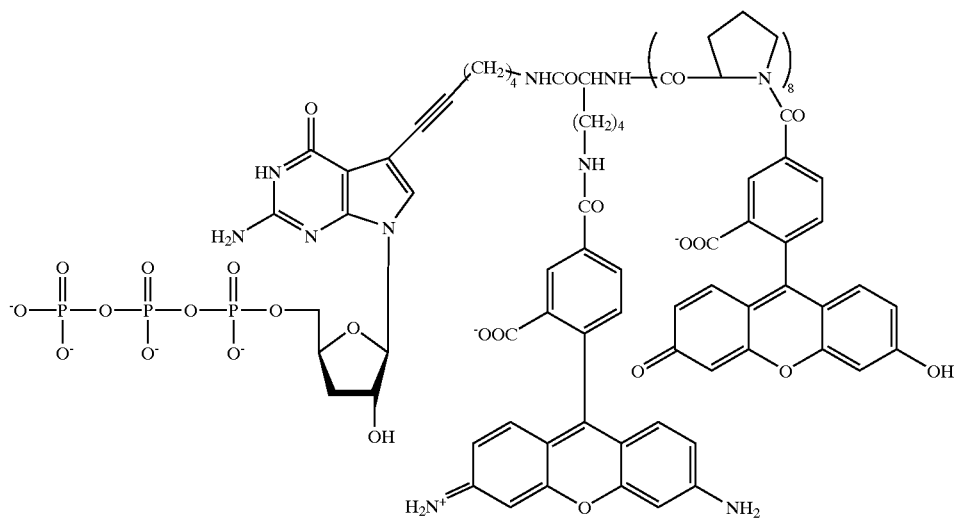

REFERENCE EXAMPLE 5

Cloning of Wild Type T7 RNA Polymerase Gene and Construction of Expression Plasmid T7 phage harbored in *E. coli* was prepared as follows. *E. coli* strain C600 was inoculated in 200 ml of LB culture medium (culture medium prepared by dissolving Bacto tryptone 10 g, Bacto yeast extract 5 g, and NaCl 5 g in 1 liter of water, which was adjusted to pH 7.5, and sterilized in an autoclave). When the cell density reached OD (600 nm)=1.0, the cells were infected with the phage at a multiplicity of infection of about 2. The OD was determined periodically, and when the OD was sharply decreased, the cell residue was removed by centrifugation. The resulting medium was added with NaCl and polyethylene glycol 6000 to final concentrations of 0.5 M and 10% respectively, stirred sufficiently, and left stand overnight to form precipitates. The precipitates were collected by centrifugation, and suspended in SM buffer (10 mM Tris-HCl, pH 7.5, 10 mM MgSO$_4$, 50 mM NaCl, 0.01% gelatin). This T7 phage concentrate was overlaid on CsCl solution layers having different concentrations, which were carefully overlaid in a centrifugation tube (CsCl solutions having concentrations of 1.267 g/ml, 0.817 g/ml, and 0.705 g/ml from the bottom layer), and centrifuged at 22,000 rpm for 2 hours to form a phage layer. A white band of the phage was carefully separated, and dialyzed against TE buffer (10 mM Tris-HCl, pH 7.5, 1 mM EDTA) to remove the CsCl component. This phage solution was treated with phenol to denature phage protein, and the genome DNA of T7 phage was purified.

Figure 2:
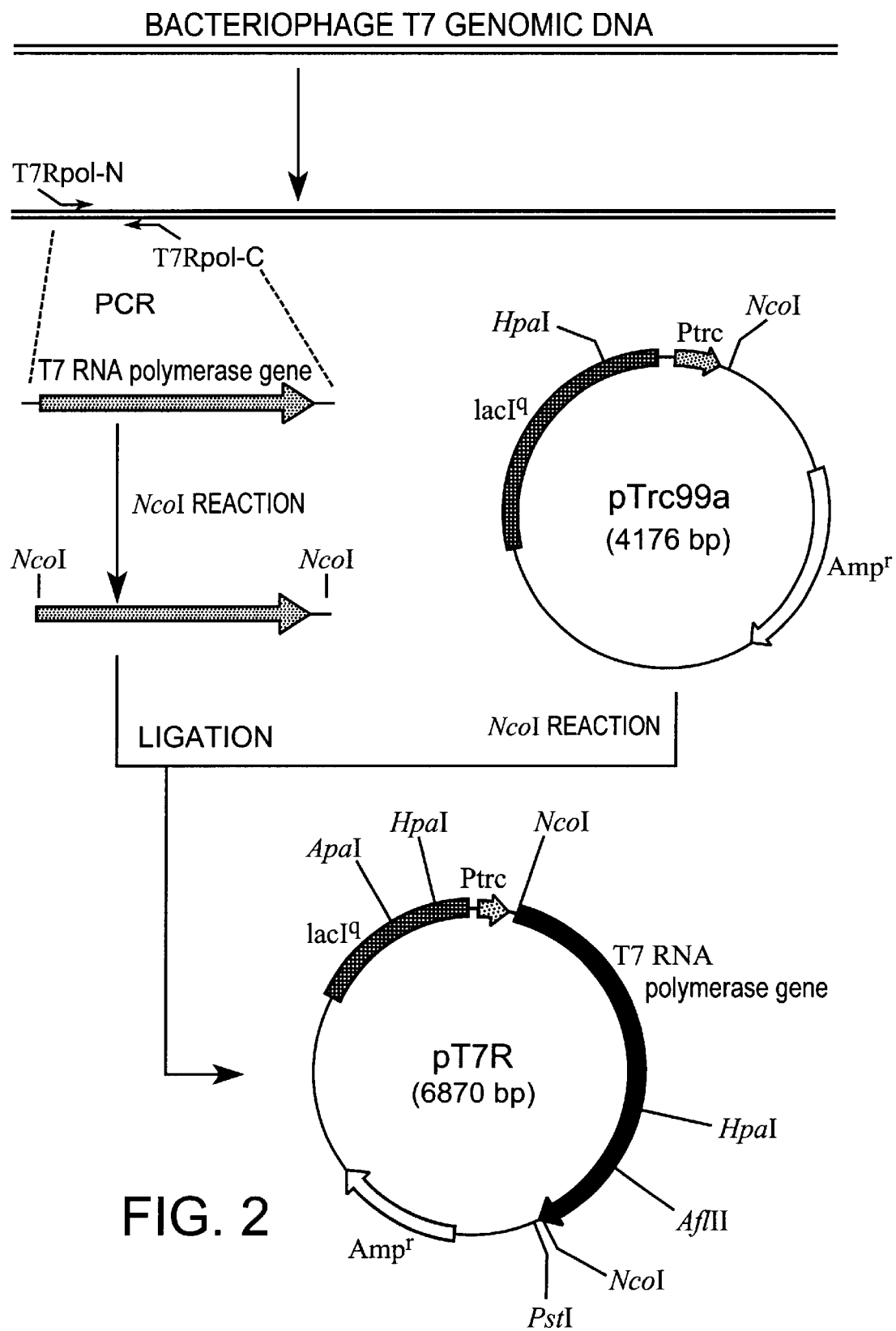
FIG. 2 shows a construction map of pT7R, a plasmid expressing wild type T7 RNA polymerase.

The T7 RNA polymerase gene corresponds to the 3171st-5822nd base pairs in the 39,937 base pairs of the genome DNA [the total nucleotide sequence of T7 genomic gene had already been reported by Dunn et al. (1983, J. Mol. Biol., 166(4):477–535), but it was slightly corrected (see T7 phage DNA sequence of GeneBank, accession No. V01148 J02518 X00411)]. This genome DNA was amplified by PCR by using it as a template, and cloned into an expression vector as follows (see FIG. 2). That is, the gene encoding the enzyme was amplified by PCR by using a primer specific for upstream of the N-terminus amino acid region of T7 RNA polymerase gene [SEQ ID NO: 1] (T7Rpol-N 5'-ATA TTT TAG CCA TGG AGG ATT GAT ATA TGA ACA CGA TTA ACA TCG CTA AG-3') and a primer specific for downstream of the C-terminus amino acid region of T7 RNA polymerase gene [SEQ ID NO: 12] (T7Rpol-C 5'-ATA TTT TAG CCA TGG TAT AGT GAG TCG TAT TGA TTT GCG-3'), each containing NcoI restriction site at the 5'-end. This DNA fragment was digested with NcoI, and separated by electrophoresis on 1% agarose gel, and the band of the objective DNA fragment was cut out from the agarose, and purified by using Gene Pure Kit (Nippon Gene). The DNA fragment was ligated to an expression vector pTrc99a (Pharmacia Biotech) which had been digested with NcoI and dephosphorylated to construct pT7R which expressed T7 RNA polymerase at high level. The plasmid pT7R expressing wild type T7 RNA polymerase was transformed into E. coli DH5α, and the E. coli cells resistant to antibiotic ampicillin was cultured. The Trc promoter contained in the expression vector pT7R was driven by adding IPTG to the culture medium. Two hours after the addition of IPTG, the E. coli cells were collected, and the total protein threrein was analyzed by SDS-polyacrylamide gel electrophoresis. As a result, a protein band was detected at a location corresponding to about 99 kDa, which is the molecular weight of T7 RNA polymerase, only when IPTG was added. This protein was further purified by a partially modified version of the previously described method of Zawadzki, V et al. 1991, Nucl. Acids Res., 19:1948 (details may be substantially the same as those of the method for purifying mutant T7 RNA polymerase exemplified in Reference Example 7), and found to have RNA polymerase activity which was exerted in a T7 promoter specific manner.

REFERENCE EXAMPLE 6

Figure 3:
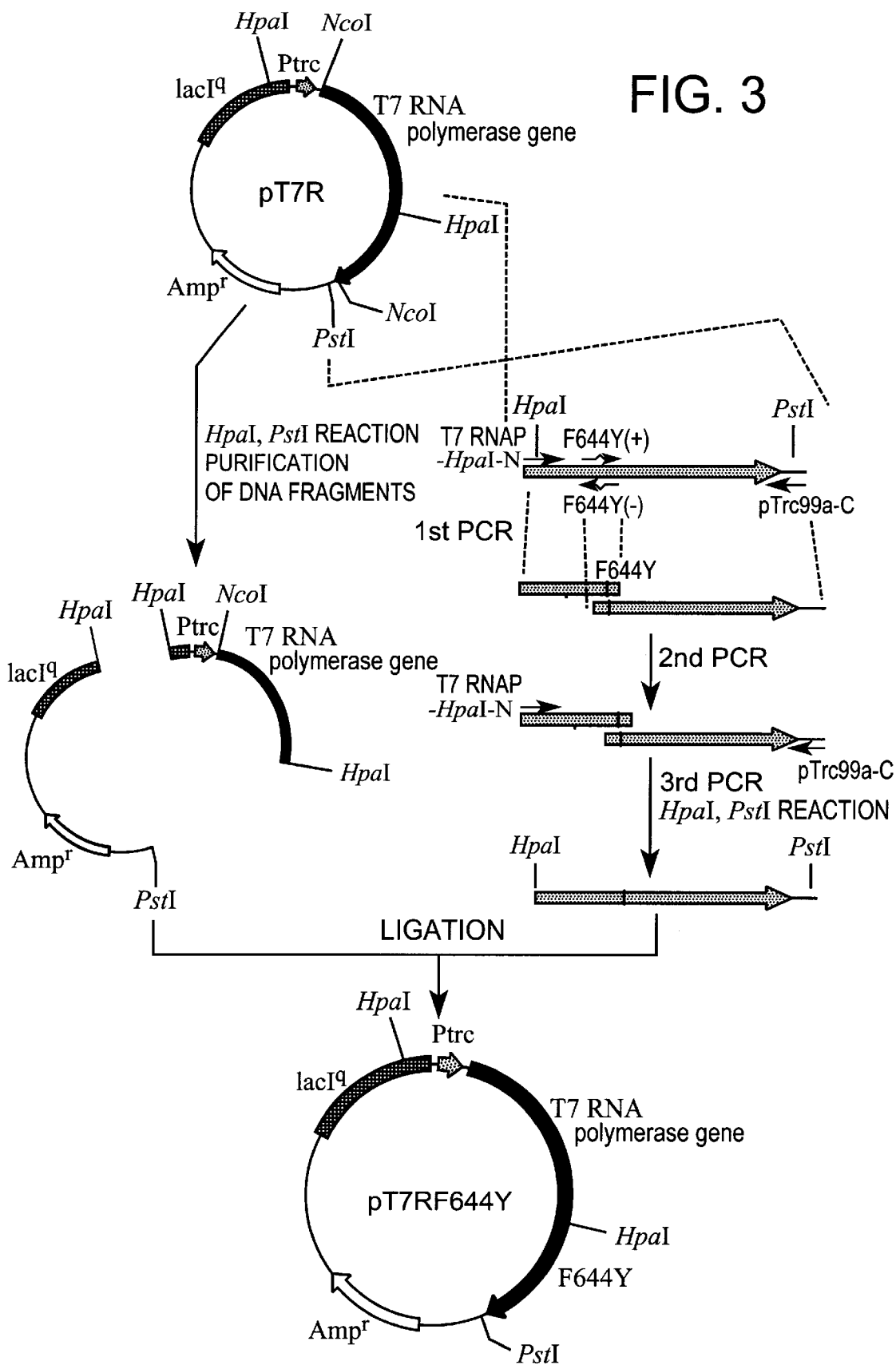
FIG. 3 shows a construction map of pT7RF644Y, a plasmid expressing a mutant T7 RNA polymerase, F644Y.

Construction of Expression Plasmid for Producing Mutant T7 RNA Polymerase (1) Construction of Expression Plasmid for Producing Mutant T7 RNA Polymerase F644Y (see FIG. 3)

By using pT7R inserted with the wild type T7 RNA polymerase gene as a template, mutation was introduced by PCR into the region between the HpaI and NcoI restriction sites corresponding to the C-terminus side of the T7 RNA polymerase gene. Moreprecisely,the region was divided into two fragments, left side and right side, at the nucleotide to be mutated, and these DNA fragments were amplified by PCR using primers [SEQ ID NOS. 3–4] F646Y(+) (5'-GTT GAC GGA AGC CGT ACT CTT TGG AC-3') introduced with a mutation and F646Y(−) (5'-GTC CAA AGA GTA CGG CTT CCG TCA AC-3'), and primers (SEQ ID NOS: (5–6) T7RNAP-HpaI-N (5'-CGC GCG GTT AAC TTG CTT CCT AG-3') and pTrc99a-PstI-C (5'-GCA TGC CTG CAG GTC GAC TCT AG-3'), containing a restriction cleavage site at the 5' end. These DNA fragments had complementary regions, and denaturation, annealing and extension reactions of the regions were repeated to prepare a DNA fragment introduced with the desired mutation. This DNA fragment was purified by collecting only a DNA fragment of a desired size through agarose gel electrophoresis, and this was re-amplified by using it as a template together with the primers T7RNAP-HpaI-N and pTrc99a-PstI-C, and cleaved with restriction endonuclease HpaI and PstI. This DNA fragment was separated by 1% agarose gel electrophoresis, and the band of the desired DNA fragment was cut out, and purified. The HpaI, PstI DNA fragment of pT7R was replaced with this DNA fragment to introduce a mutation. The resulting pT7R was transformed into E. coli DH5α, and cells harboring the plasmid introduced with the mutation were selected. Finally, the nucleotide sequence was determined to confirm whether the mutation was introduced into the desired site. Thus, the expression plasmid pT7RF644Y for producing mutant T7 RNA polymerase F644Y was obtained. For the production of the mutant T7 RNA polymerase F644Y from this plasmid, expression could be induced by adding IPTG to the cultured E. coli cells harboring the plasmid, like the production of wild type T7 RNA polymerase.

Figure 4:
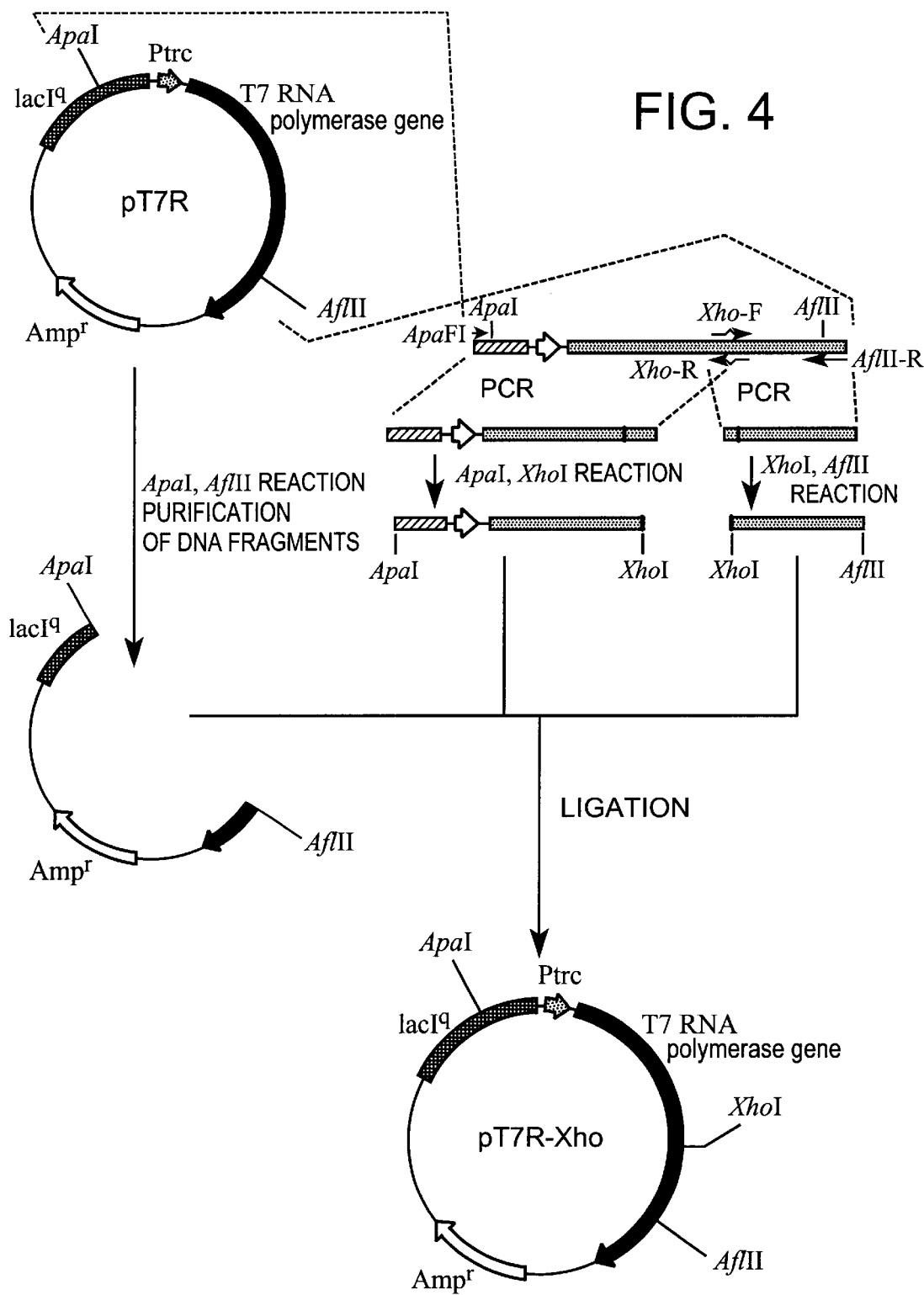
FIG. 4 shows a construction map of pT7R-Xho, an improved version of the plasmid pT7R, which has a restriction endonuclease XhoI site in the T7 RNA polymerase gene.
Figure 5:
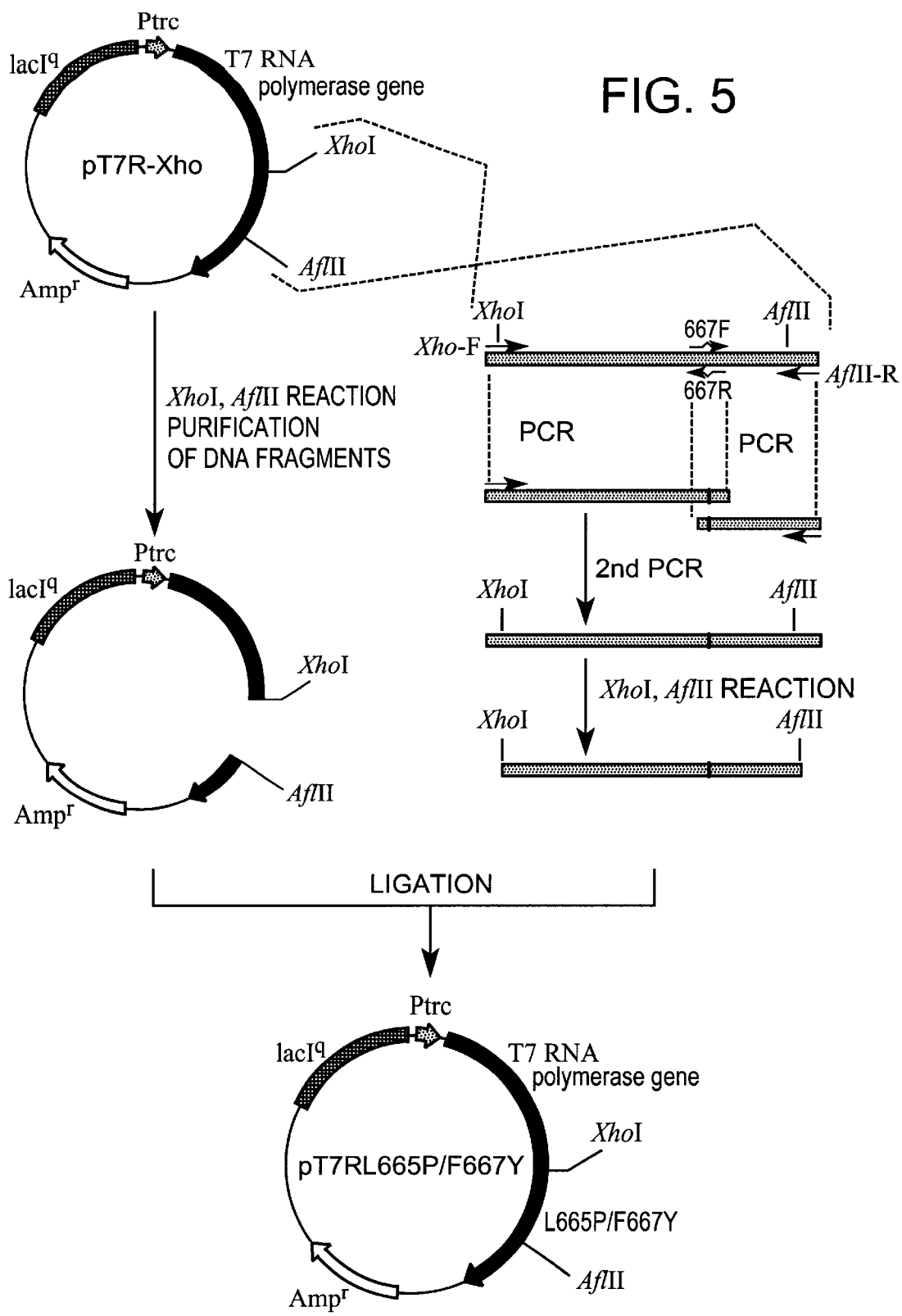
FIG. 5 shows a construction map of pT7RL665P/F667Y, a plasmid expressing a mutant T7 RNA polymerase, L665P/F667Y.

(2) Construction of Expression Plasmid for Producing Mutant T7 RNA Polymerase L665P/F677Y (see FIGS. 4 and 5)

The construction of mutant T7 RNA polymerase L665P/F667Y was performed as follows based on PCR technique as in the construction of the F644Y mentioned above.

First, a XhoI restriction site (CTCGAG) was introduced into the T7 RNA polymerase gene region of the expression vector pT7R having the wild type T7 RNA polymerase gene to facilitate the introduction of mutation. More specifically, the expression vector pT7R used as a template was amplified by using a primer pair of primer (SEQ ID NO: 7) ApaF1 (5'-CAT CTG GTC GCA TTG GGT CAC-3') and primer (SEQ ID NO: 8) Xho-R (5'-CCAAGT GTT CTC GAG TGG AGA-3'), and a primer pair of a primer (SEQ ID NO: 9) Xho-F (5-CTA AGT CTC CAC TCG AGA ACA CTT GG-3') and a primer (SEQ ID NO: 10) AflII-R (5'-CAG CCA GCA GCT TAG CAG CAG-3'), respectively. The former amplified DNA fragment was digested with restriction endonucleases ApaI and XhoI, and the latter amplified DNA fragment with restriction endonucleases AflII and XhoI, and they were ligated to the expression vector pT7R preliminarily treated with ApaI and AflII by using T4 DNA ligase.

This reaction product was transformed into E. coli DH5α, and several colonies grown on an agar plate containing antibiotic ampicillin were obtained. Some of these colonies were selected and cultured, and plasmid DNA was extracted from the cultured cells to obtain plasmid pT7R-Xho in which a XhoI restriction site was introduced in the T7 RNA polymerase gene region (see FIG. 4). Presence of this XhoI site can be confirmed by cleavage produced by a treatment with the restriction endonuclease XhoI, and nucleotide sequencing of the DNA. Using this plasmid pT7R-Xho as a template, PCR was performed with a primer (SEQ ID NO: 11) pair of primer Xho-R and primer 667R (5'-GCT GAG TGT ACA TCG GAC CCT-3'), and a primer pair of a primer (SEQ ID NO: 12)667F (5'-GCT GAG TGT ACA TCG GAC CCT-3') and a primer AflIIR. The PCR products were directly used as templates for the nucleotide sequencing of the DNA to determine the sequences of the primers 667R and 667F. Then, they were subjected to electrophoresis on 2% agarose gel (Agarose X from Nippon Gene was used as the agarose), respectively, and bands corresponding to DNA fragments of the desired sizes were cut out to purify the DNA fragments by using Gene Pure Kit. The purified two kinds of DNA fragments were mixed, and used as templates for PCR using the primers XhoF and AflIIR. After confirming that the amplified DNA fragment was the desired fragment by restriction endonuclease mapping and DNA sequencing, the fragment was digested with restriction endonucleases XhoI and AflII, and the resulting fragment was ligated to the plasmid pT7R-Xho preliminarily treated with restriction endonucleases XhoI and AflII by using T4 DNA ligase. This reaction product was transformed into E. Coli DH5α, and several colonies of the cells grown on an agar plate containing antibiotic ampicillin were obtained. Some of these colonies were selected and cultured, and plasmid DNA was extracted from the cultured cells. The plasmid DNA was confirmed if it was introduced with the desired mutation or not by DNA sequencing, and finally construct an expression plasmid pT7RL665P/F667Y for producing desired mutant T7 RNA polymerase L665P/F667Y (see FIG. 5). For the production of the mutant T7 RNA polymerase L665P/F667Y from this plasmid, expression could be induced by adding IPTG to the cultured E. coli cells harboring the plasmid, like the production of wild type T7 RNA polymerase.

REFERENCE EXAMPLE 7

Purification of Mutant T7 RNA Polymerases

Mutant T7 RNA polymerase proteins introduced into E. coli were purified.

Wild types of this protein have already been described in Chamberlin, M et al. Nature, 228:227–231(1970), and Davanloo et al., Proc. Natl. Acad. Sci. USA., 81:2035–2039 (1984). Its large scale production has also been reported by Zawadzki, V et al., Nucl. Acids Res., 19:1948 (1991).

All of the mutant T7 RNA polymerases can be purified principally by the same method. The difference of mutation site may cause some difference in the expression level, and behavior in column chromatography. The purification method of mutant T7 RNA polymerase F644Y is exemplified hereinafter. The expression vector pT7RF644Y for F644Y was introduced into E. coli DH5α, and the cells were cultured in a test tube containing LB culture medium containing antibiotic ampicillin. When the OD (600 nm) of the medium reached 0.4–0.6, isopropyl-β-thiogalactopyranoside (IPTG) was added to the culture to a final concentration of 0.4 mM, and the cultivation was further continued for additional 8 hours. Then, the E. coli cells were collected by centrifugation. Typically, 2 liters of culture medium affords 10 g of E. coli cells in wet weight. If the E. coli cells are not used immediately, they can be stored in a refrigerator at −20° C.

All of the subsequent steps for purification of enzyme should be performed at a temperature lower than room temperature, preferably 0–5° C. unless otherwise indicated. The E. coli cells were washed with tenfold amount relative to the cell weight of a washing buffer (20 mM Tris-HCl, pH8.1, 130 mM NaCl, 2 mM EDTANa$_2$ at 25° C.), centrifuged again (5,000×g, 4° C., 10 minutes), suspended in tenfold in volume of a sonication buffer [50 mM Tris-HCl, pH 8.1, 100 mM NaCl, 0.1 mM EDTANa$_2$,5 mM dithiothreitol (DTT), 0.1 mM benzamidine, 30 µg/ml phenylmethylsulfonyl fluoride (PMSF), 10 µg/ml bacitracin], and sonicated by using Sonifier 450 (Branson) at 80 W for 15 minutes to destroy the cells and reduce the viscosity of the cells. Then, the cell suspension was centrifuged at 12,000×g at 4° C. for ten minutes to remove the cell debris. 10% streptomycin sulfate was slowly added dropwise to the resulting supernatant to a final concentration of 2.0% with stirring, and stirring was further continued for 30 minutes. The resulting supernatant was centrifuged at 12,000×g at 4° C. for ten minutes to remove precipitates, and slowly added with ammonium sulfate powder with stirring to form precipitates. In this case, precipitates were first collected by 30% saturated ammonium sulfate (30% ammonium sulfate precipitation), and the resulting supernatant was further added with ammonium sulfate to 60% saturation with stirring to form precipitates again (30–60% ammonium sulfate precipitation). The supernatant was added again with ammonium sulfate powder to 90% ammonium sulfate saturation, and stirred at 4° C. for 1 hour, and the precipitates were collected by centrifugation. Proteins in aliquots of these three ammonium sulfate fractions were analyzed by SDS-acrylamide gel electrophoresis, and it was found that most of the objective mutant T7 RNA polymerase was present in the 30–60% ammonium sulfate fraction. Therefore, purification was performed hereafter by using this fraction. The 30–60% ammonium sulfate fraction was suspended in a small amount of column buffer (20 mM KPO$_4$, pH 7.7, 100 mM NaCl, 1 mM DTT, 30 µg/ml PMSF), and desalted by dialysis against 500 ml of the same buffer for 16 hours. The dialysate was applied on a heparin-Sepharose column of 5 ml volume (Pharmacia Biotech). Subsequently, the column was washed with the same buffer until any material absorbing ultraviolet ray at 280 nm disappeared, and eluted with a linear gradient of 0.1 M to 0.64 M NaCl in the same buffer of about 40-fold volume of the column volume.

The eluent was collected in test tubes as fractions of a suitable volume, and immediately subjected to SDS-acrylamide gel electrophoresis for protein analysis to identify fractions containing proteins around a molecular weight considered to be of the objective mutant T7 RNA polymerase. In typical examples, it should be found around 0.4 M NaCl. The fractions containing the protein were collected, and desalted by dialysis against about 1 liter of the column buffer (20 mM KPO$_4$, pH 7.7, 100 mM NaCl, 1 mM DTT, 30 µg/ml PMSF) for 16 hours. The fractions desalted by dialysis were applied to a Q-Sepharose column (Pharmacia Biotech) of 5 ml volume that preliminarily equilibrated with the same buffer, and the column was washed with the same buffer until any material absorbing ultraviolet ray at 280 nm disappeared, and eluted with a linear gradient of 0.1 M to 0.64 M NaCl in the same buffer of about 40-fold volume of the column volume. The eluent was collected in test tubes as fractions of a suitable volume, and immediately subjected to SDS-acrylamide gel electrophoresis for protein analysis to identify fractions containing proteins around a molecular weight considered to be of the objective mutant T7 RNA polymerase. In typical examples, it should be found around 0.24 M NaCl. The fractions containing the protein were collected, dialyzed against 500 ml of storage buffer (50% glycerol, 20 mM KPO$_4$, pH 7.7, 100 mM NaCl, 1 mM DTT, 30 µg/ml PMSF) for 16 hours, and stored at −20° C. until use. In vitro RNA synthesis activity and activity of the contaminated ribonuclease of this sample in the state of storage were examined. The in vitro RNA synthesis activity was examined by, for example, performing RNA synthesis reaction according to the enzyme dilution method using the plasmid containing T7 promoter as a template and a commercially available wild type T7 RNA polymerase (BRL, Gibco) as a standard, and subjecting the synthesized RNA to agarose gel electrophoresis to estimate approximate titer. In this case, because degree of decomposition of RNA is also determined, simple assay for contaminated ribonuclease can simultaneously be performed. As a typical example, 2,500,000 units of the mutant T7 RNA polymerase F644Y protein was purified from 1 liter of culture medium by purification using the above-described steps, and this preparation was substantially free from RNase contamination.

REFERENCE EXAMPLE 8

Purification of Inorganic Pyrophosphatase Free from RNase Activity

Inorganic pyrophosphatase (PPase) free from RNase was produced as follows, but its production method is not limited to the method described below.

As a starting material of the production of inorganic pyrophosphatase, a roughly purified product derived from yeast, which was available from Sigma (Sigma I-1643, EC.3.6.1.1), was used, and 4 mg (680 units) of the product was suspended in a buffer (20 mM Tris-HCl, 1 mM EDTA, pH 7.9, 1 ml), and dialyzed against the same buffer for two hours for desalting, and the dialysate was subjected to column chromatography in an SP Sepharose column having a column volume of 1 ml (Pharmacia Biotech). More specifically, the column was sufficiently washed with the same buffer of about 20-fold volume of the column volume until many material absorbing ultraviolet ray at 280 nm disappeared, and eluted with a linear gradient of 0 to 0.1 M NaCl in the same buffer of about 20-fold volume of the column volume. The eluent was collected in test tubes as fractions of a suitable volume, and immediately subjected to SDS-12.5% polyacrylamide gel electrophoresis to identify fractions containing a protein of 32 kDa. In typical examples, the PPase fractions should be found in the unabsorbed portion. The fractions containing the protein were collected, absorbed by Q-Sepharose column (Pharmacia Biotech) having a column volume of 1 ml, and eluted with a linear gradient of 0 to 0.1 M NaCl in the same buffer of about 20-fold volume of the column volume. The eluent was collected as fractions of a suitable volume, and immediately subjected to SDS-12.5% polyacrylamide gel electrophoresis to identify fractions containing a protein of 32 kDa. In typical examples, it should be found around 0.35 M NaCl. The fractions containing the protein of 32 kDa were collected, dialyzed against 500 ml of storage buffer (20 mM Tris-HCl, 1 mM EDTA, 50% glycerol, pH 7.9) for 16 hours, and stored at −20° C. until use. In typical examples, a specimen containing 425 units of the PPase protein, i.e., 0.425 units/$\mu$l, could be obtained with a collection yield of 62.5%.

RNase contamination degree of the above specimen was examined by using 8 $\mu$g of $E.$ $coli$ rRNA (16S and 23S) as substrates. More specifically, the PPase in an amount corresponding to 0.17 units was added to the $E.$ $coli$ rRNA in a buffer containing 8 mM MgCl$_2$, 2 mM spermidine-(HCl)$_3$, 5 mM DTT, 40 mM Tris/HCl, pH 8.0, and allowed to react at 37° C. for four hours. The RNA was subjected to 1.0% agarose gel electrophoresis under a denaturation condition where formamide was present, and electrophoresis was finished when simultaneously added xylenecyanol dye reached the height of about ⅓ of the agarose gel. The gel was irradiated with ultraviolet light (wavelength: 254 nm), and photographed to examine degree of the RNA degradation. The PPase in the roughly purified product and the PPase after purification were compared, and degradation of RNA was observed in the roughly purified product, whereas significant RNA degradation activity was not observed in the purified product.

EXAMPLE 5

Comparison of sequencing reactions utilizing energy transfer terminators and conventional dye terminators in in vitro transcription reaction using mutant RNA polymerase Effect of the energy transfer terminators of 3'-dNTP on nucleotide sequencing methods was examined by in vitro genetic transcription using the mutant T7 RNA polymerase F644Y. As the sequencing reaction, the method described by Melton, D. A. (1984, Nucleic Acids Res., 12: 7035–7056) was used. More specifically, a plasmid vector pBluescriptKS (+) having T7 promoter (Stratagene) was linearized by digestion with restriction endonuclease PvuII, and used as a template. As the energy transfer terminator derivatives of 3'-dNTP, the dye terminators having a proline spacer, which were the compounds 10–13 synthesized in Examples 1–4, were used. Specifically, the reaction was performed in a system of a total reaction volume of 10 $\mu$l containing 4 $\mu$M FAM and R6G-labeled 3'-dATP, 4 $\mu$M FAM and R110-labeled 3'-dGTP, 80 $\mu$M FAM and XR-labeled 3'-dCTP and 20 $\mu$M FAM and TMR-labeled 3'-dUTP, 500 $\mu$M GTP and UTP, and 250 $\mu$M ATP and CTP, 8 mM MgCl$_2$, 2 mM spermidine-(HCl)$_3$, 5 mM DTT, and 40 mM Tris/HCl, pH 8.0 (BRL, Gibco), added with the mutant T7 RNA polymerase F644Y (25 U), and inorganic pyrophosphatase derived from yeast (0.045 U) at 37° C. for one hour.

For comparison, reaction utilizing dye terminators having only one fluorescent dye was similarly performed in a system of a total reaction volume of 10 $\mu$l containing 4 $\mu$M R6G-4x-3'-dATP, 4 $\mu$M R110-4x-3'-dGTP, 80 $\mu$M XR-4x-3'-dCTP, 20 $\mu$M TMR-4x-3'-dUTP, 500 $\mu$M GTP and UTP, 250 $\mu$M ATP and CTP, 8 mM MgCl$_2$, 2 mM spermidine-(HCl)$_3$, 5 mM DTT, and 40 mM Tris/HCl, pH 8.0 (BRL, Gibco), added with the mutant T7 RNA polymerase F644Y (25 U), and inorganic pyrophosphatase derived from yeast (0.05 U) at 37° C. for one hour. Then, to remove the unreacted terminators remained in the reaction products, the transcription products were purified by gel filtration using a Sephadex G-50 column (Pharmacia Biotech), and the purification products were evaporated to dryness using a centrifugal evaporator.

Each dried reaction product was dissolved in 6 $\mu$l of formamide/EDTA/Blue dextran loading buffer, and 2 $\mu$l of the solution was analyzed by ABI 377 DNA Sequencer and an analysis program (Sequencing Analysis Ver. 3.0) using denatured gel for sequencing analysis which contained 6M urea/4% Long Ranger™ acrylamide solution (FMC) according to the instruction manual Ver.1.0 of ABI PRISM 377 DNA Sequencing System available from ABI (Perkin-Elmer Corporation, Applied Biosystems Division).

As a result, it was found that use of the energy transfer terminators afforded stronger intensity of sequence ladders. Therefore, the reaction products were diluted with formamide/EDTA/Blue dextrane loading buffer, and 2 $\mu$l of the diluted reaction products were subjected to electrophoresis. As a result, it was found that 10-fold dilution enables sequencing with approximately the same peak intensity as that obtained with conventional dye terminators. Comparison of a typical sequencing pattern obtained with 10-fold dilution of the energy transfer terminators and a sequence pattern obtained with conventional dye terminators was shown in FIG. 1. From these results, it was found that the energy transfer terminators enable sequencing with tenfold higher sensitivity compared with the conventional dye terminators.

When the sequencing was performed by using the mutant T7 RNA polymerase L665P/F667Y instead of the mutant T7 RNA polymerase F644Y, results similar to the above were obtained.

The chemical structures of R6G-4x-3'-dATP (14), R100-4x-3'-dGTP (15), XR-4x-3'-dCTP (16) and TMR-4x-3'-dUTP (17) used above are shown below.

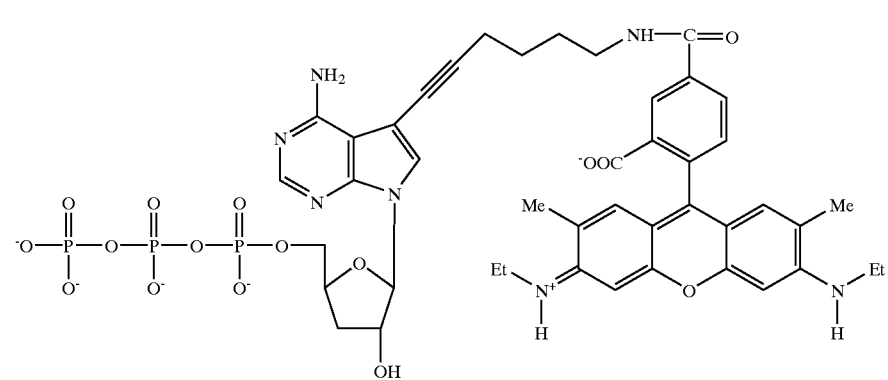
(14)
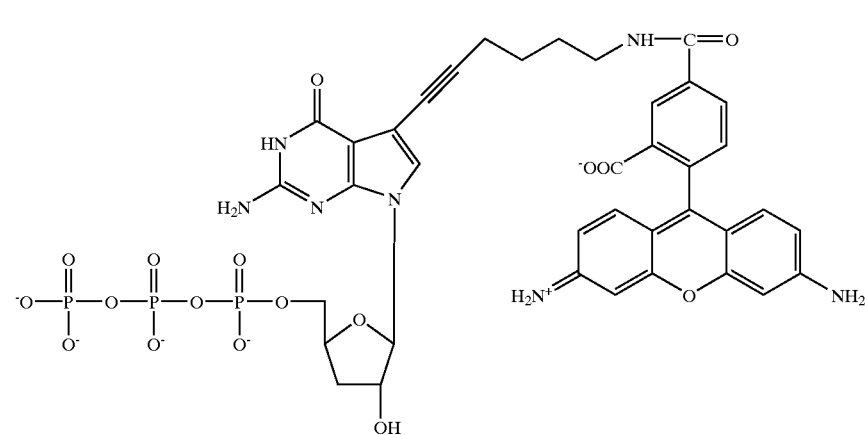
(15)
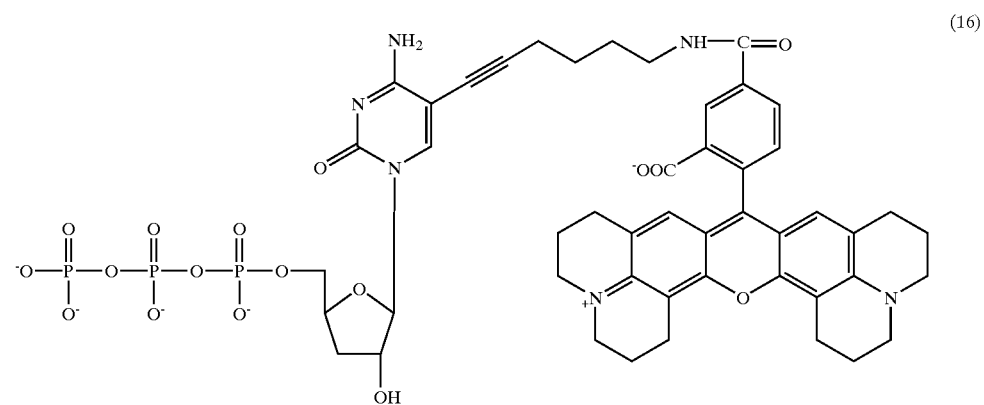
(16)
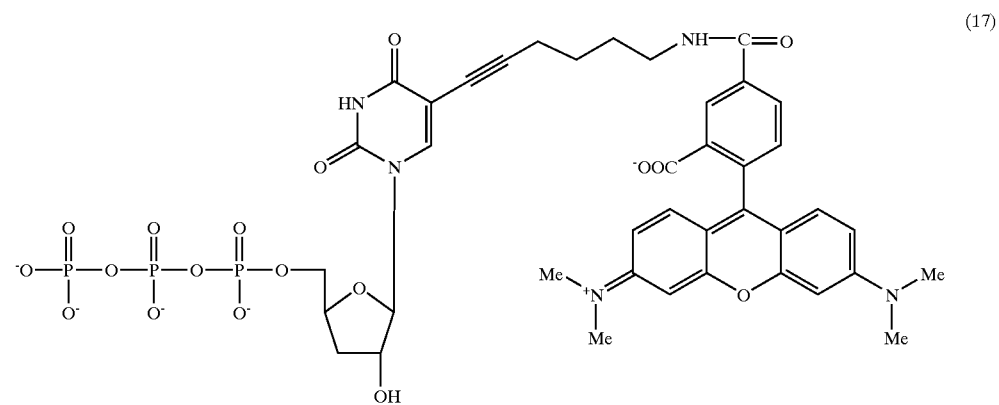
(17)

What is claimed is:

1. A compound represented by the following general formula (1):

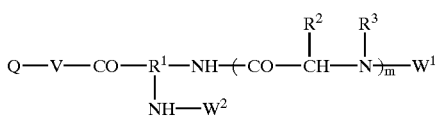

wherein Q represents a mono- or oligonucleotide residue, V represents $-C\equiv C-(CH_2)_{n1}-NH-$ or $-CH=CH-(CH_2)_{n2}-NH-$, wherein n1 and n2 represent an integer not less than 1, $R^1$ represents a trivalent group, $R^2$ and $R^3$ independently represent hydrogen atom or a hydrocarbon residue, or $R^2$ and $R^3$ may join to form a ring together with the adjacent CH and NH, $W^1$ and $W^2$ independently represent a fluorescent group, and m represents an integer not less than 1.

2. The compound of claim 1, wherein $R^1$ represents

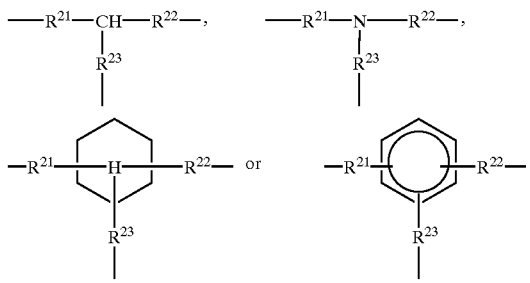

wherein $R^{21}$-$R^{23}$ independently represent a single bond or a divalent hydrocarbon residue.

3. The compound of claim 1, wherein $R^2$, $R^3$ and m are selected so that the distance between $W^1$ and $W^2$ should be within the range of 10–100 Å.

4. The compound of claim 1, wherein Q is a 2',3'-dideoxyribonucleotide residue or a 3'-deoxyribonucleotide residue.

5. A terminator which is the compound of claim 4 and used for a DNA sequence determination method based on the chain terminator method.

6. A method for determining DNA sequences based on the chain terminator method characterized in that the chain termination reaction is performed by using the compound of claim 4 as a terminator.

7. The method of claim 6, wherein the compound in which Q is a 2',3'-dideoxyribonucleotide residue is used as a terminator, and a DNA polymerase is used.

8. The method of claim 6, wherein the compound in which Q is a 3'-deoxyribonucleotide residue is used as a terminator, and an RNA polymerase is used.

9. The method of claim 6, wherein four kinds of compounds corresponding to four kinds of bases are used as terminators, provided that the compounds are selected from the compounds of claim 4 and each of which has one of different four kinds of fluorescent groups as at least one of $W^1$ and $W^2$, and the chain termination reaction using the four kinds of compounds is performed in the same reaction system.

10. The compound of claim 1, wherein Q is an oligonucleotide residue having a 2'-deoxyribonucleotide residue at its end.

11. A primer which is the compound of claim 10 and is used in a DNA sequence determination method based on the primer method.

12. A method for determining DNA sequences based on the primer method characterized in that the compound of claim 10 is used as a primer.

13. The compound of claim 1, wherein Q is a mono- or oligonucleotide residue not having a phosphate group, or having a mono- or diphosphate group at the 5' end.

14. An initiator which is the compound of claim 13 and is used in a DNA sequence determination method based on the chain terminator method.

15. A method for determining DNA sequences based on the chain terminator method characterized in that the chain termination reaction is performed by using an initiator, wherein said initiator is a mono- or oligonucleotide residue not having a phosphate group, or having a mono- or diphosphate group at the 5' end with two kinds of reporters attached that are a donor and an acceptor of energy transfer, and an RNA polymerase.

16. The method of claim 12, wherein an unlabeled terminator is used as a terminator.

17. A method for determining DNA sequences based on the chain terminator method characterized in that the chain termination reaction is performed by using a terminator, wherein said terminator is a 3'-deoxyribonucleotide residue with two kinds of reporters attached that are a donor and an acceptor of energy transfer, and an RNA polymerase.

18. The method of claim 17, wherein the two kinds of reporters contained in the terminator are arranged with a distance sufficient for causing energy transfer from the donor to the acceptor.

19. The method of claim 18, wherein the distance sufficient for causing energy transfer from the donor to the acceptor is in the range of 10–100 Å.

20. The method of claim 17, wherein the reporters are selected from the group consisting of fluorescent groups, phosphorescent groups, spin-labeled groups and groups having high electron density.

21. The method of claim 17, wherein the donor is selected from the group consisting of fluorescein dyes, rhodamine dyes and 4,4-difluoro-4-bora-3a,4a-diaza-s-indacene dyes, and the acceptor is selected from the group consisting of fluorescein dyes, rhodamine dyes and 4,4-difluoro-4-bora-3a,4a-diaza-s-indacene dyes.

22. The method of claim 17, wherein four kinds of terminators corresponding to the four kinds of bases are used, provided that each of which terminators has one of different four kinds of reporters as the acceptor, and the chain termination reaction using the above four kinds of terminators is performed in the same reaction system.

23. The method of claim 6, wherein the chain termination reaction is performed in the presence of inorganic pyrophosphatase.

24. The compound of claim 2, wherein $R^2$, $R^3$ and m are selected so that the distance between $W^1$ and $W^2$ should be within the range of 10–100 Å.

25. The compound of claim 2, wherein Q is a 2',3'-dideoxyribonucleotide residue or a 3'-deoxyribonucleotide residue.

26. A terminator which is the compound of claim 25 and used for a DNA sequence determination method based on the chain terminator method.

27. A method for determining DNA sequences based on the chain terminator method characterized in that the chain termination reaction is performed by using the compound of claim 26 as a terminator.

28. The method of claim 25, wherein the compound in which Q is a 2',3'-dideoxyribonucleotide residue is used as a terminator, and a DNA polymerase is used.

29. The method of claim 25, wherein the compound in which Q is a 3'-deoxyribonucleotide residue is used as a terminator, and an RNA polymerase is used.

30. The method of claim 7, wherein the chain termination reaction is performed in the presence of inorganic pyrophosphatase.

31. The method of claim 7, wherein the chain termination reaction is performed in the presence of inorganic pyrophosphatase.

32. The method of claim 15, wherein the chain termination reaction is performed in the presence of inorganic pyrophosphatase.

33. The method of claim 15, wherein an unlabeled terminator is used as a terminator.

34. The method of claim 18, wherein the chain termination reaction is performed in the presence of inorganic pyrophosphatase.

35. A method for determining DNA sequences based on the chain terminator method, wherein the chain termination reaction is performed by using an initiator and two kinds of reporters that can be a donor and an acceptor of energy transfer, and an RNA polymerase, wherein the initiator is a compound represented by the following general formula

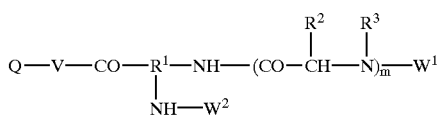

(1)

wherein Q is a mono- or oligonucleotide residue not having a phosphate group, or having a mono- or diphosphate group at the 5' end;

V represents $—C\equiv C—(CH_2)_{n1}—NH—$ or $—C=C—(CH_2)_{n2}—NH—$, wherein n1 and n2 represent an integer not less than 1, $R^1$ represents a trivalent group, $R^2$ and $R^3$ independently represent hydrogen atom or a hydrocarbon residue, or $R^2$ and $R^3$ may join to form a ring together with the adjacent CH and NH, $W^1$ and $W^2$ independently represent a fluorescent group, and m represents an integer not less than 1.

36. The method according to claim 35, wherein $R^2$, $R^3$, and m are selected so that the distance between $W^1$ and $W^2$ should be within the range of 10–100 Å.

37. A method for determining DNA sequences based on the chain terminator method, wherein the chain termination reaction is performed by using an initiator and two kinds of reporters that can be a donor and an acceptor of energy transfer, and an RNA polymerase, wherein the initiator is a compound represented by the following general formula

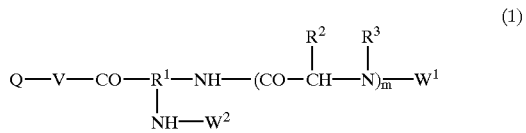

(1)

wherein Q is a mono- or oligonucleotide residue not having a phosphate group, or having a mono- or diphosphate group at the 5' end;

V represents $—C\equiv C—(CH_2)_{n1}—NH—$ or $—C=C—(CH_2)_{n2}—NH—$, wherein n1 and n2 represent an integer not less than 1, $R^1$ represents

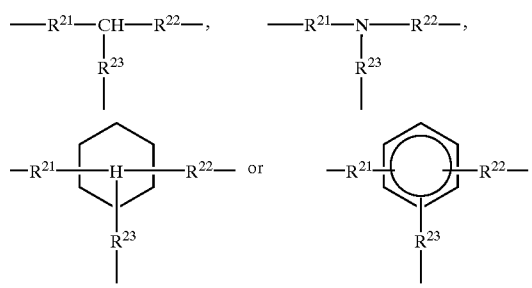

wherein $R^{21}$, $R^{22}$, and $R^{23}$ independently represent a single bond or a divalent hydrocarbon residue, $R^2$ and $R^3$ independently represent hydrogen atom or a hydrocarbon residue, or $R^2$ and $R^3$ may join to form a ring together with the adjacent CH and NH, $W^1$ and $W^2$ independently represent a fluorescent group, and m represents an integer not less than 1.

38. The method according to claim 37, wherein $R^2$, $R^3$, and m are selected so that the distance between $W^1$ and $W^2$ should be within the range of 10–100 Å.

39. The method of claim 15, wherein the reporters are fluorescent groups, and the determination of nucleotide sequences is performed by detecting the fluorescence signal based on fluorescent groups of the reporters.

40. The method of claim 17, wherein the reporters are fluorescent groups, and the determination of nucleotide sequences is performed by detecting the fluorescence signal based on fluorescent groups of the reporters.

* * * * *